(12) United States Patent
Johnston et al.

(10) Patent No.: US 6,531,206 B2
(45) Date of Patent: Mar. 11, 2003

(54) MICROSTRUCTURED SURFACE FILM ASSEMBLY FOR LIQUID ACQUISITION AND TRANSPORT

(75) Inventors: Raymond P. Johnston, Lake Elmo, MN (US); Sara B. Mortenson, St. Louis Park, MN (US); Douglas A. Huntley, Maplewood, MN (US); Stephanie B. Castiglione, Hudson, WI (US)

(73) Assignee: 3M Innovative Properties Company, St. Paul, MN (US)

( * ) Notice: Subject to any disclaimer, the term of this patent is extended or adjusted under 35 U.S.C. 154(b) by 178 days.

(21) Appl. No.: 09/778,524

(22) Filed: Feb. 7, 2001

(65) Prior Publication Data

US 2002/0146540 A1 Oct. 10, 2002

(51) Int. Cl.[7] .............................. B32B 3/00; B32B 3/02
(52) U.S. Cl. ..................... 428/172; 428/95; 428/166; 428/167; 428/188
(58) Field of Search .................. 428/50, 95, 137, 428/166, 167, 172, 343, 354, 188; 52/390, 391

(56) References Cited

U.S. PATENT DOCUMENTS

| | | | |
|---|---|---|---|
| 2,915,554 A | 12/1959 | Ahlbrecht et al. | 260/556 |
| RE24,906 E | 12/1960 | Ulrich | 206/59 |
| 3,384,154 A | 5/1968 | Milton | |
| 3,395,903 A | 8/1968 | Norback et al. | 261/112 |
| 3,415,502 A | 12/1968 | Munters | |
| 3,455,376 A | 7/1969 | Beurtheret | |
| 3,500,615 A | 3/1970 | Meek | 55/233 |
| 3,520,300 A | 7/1970 | Flower, Jr. | 128/276 |
| 3,792,841 A | 2/1974 | Munters | 261/112 |
| 4,310,509 A | 1/1982 | Berglund et al. | 424/28 |
| 4,323,557 A | 4/1982 | Rosso et al. | 424/28 |

(List continued on next page.)

FOREIGN PATENT DOCUMENTS

| | | |
|---|---|---|
| DE | 4003875 | 8/1991 |
| EP | 0 145 867 A2 | 6/1985 |
| EP | 0 819 908 A2 | 1/1998 |
| WO | WO 91/11252 | 8/1991 |
| WO | WO 93/11727 | 6/1993 |
| WO | WO 96/04123 | 2/1996 |
| WO | WO 97/23571 | 7/1997 |
| WO | WO 99/06589 | 2/1999 |
| WO | WO 99/28128 | 6/1999 |
| WO | WO 99/65542 | 12/1999 |
| WO | WO 99/65593 | 12/1999 |
| WO | WO 99/65595 | 12/1999 |
| WO | WO 99/65664 | 12/1999 |
| WO | WO 99/65704 | 12/1999 |
| WO | WO 99/66282 | 12/1999 |
| WO | WO 00/42958 A1 | 7/2000 |
| WO | WO 01/02093 A2 | 1/2001 |

OTHER PUBLICATIONS

U.S. Ser. No. 09/570785, Bommarito et al, filed May 15, 2000.

Primary Examiner—Donald J. Loney

(57) ABSTRACT

A film or tape has one of its major surfaces defined by microstructured features including a plurality of channels defined by spaced apart protrusions. The microstructured film is able to acquire liquids and to control the directional transport of such liquids for subsequent removal therefrom. The transport can be passive or active (i.e., caused or enhanced by an applied potential). The inventive microstructured films and tapes have applications in laminate floor assemblies (for spill removal) and industrial articles such as computer keyboards and other devices and assemblies that benefit from fluid removal. The invention also has application in evaporative and condensation applications. In one embodiment, at least one cross-channel is formed on the microstructured surface to join adjacent channels for liquid flow therebetween.

20 Claims, 15 Drawing Sheets

U.S. PATENT DOCUMENTS

| | | | |
|---|---|---|---|
| 4,472,480 A | 9/1984 | Olson | 428/332 |
| 4,533,352 A | 8/1985 | Van Beek et al. | 604/317 |
| 4,679,590 A | 7/1987 | Hergenroeder | 137/602 |
| 4,747,166 A | 5/1988 | Kuntz | 4/144.1 |
| 4,917,933 A * | 4/1990 | Schluter | 428/172 |
| 4,945,697 A | 8/1990 | Ott et al. | |
| 4,986,496 A | 1/1991 | Marentic et al. | 244/130 |
| 5,055,239 A | 10/1991 | Thomas | 261/112.2 |
| 5,069,403 A | 12/1991 | Marentic et al. | 244/130 |
| 5,158,557 A | 10/1992 | Noreen et al. | 604/389 |
| 5,349,965 A | 9/1994 | McCarver | 128/846 |
| 5,437,651 A | 8/1995 | Todd et al. | 604/313 |
| 5,514,120 A | 5/1996 | Johnston et al. | 604/378 |
| 5,585,186 A | 12/1996 | Scholz et al. | 428/412 |
| 5,606,201 A | 2/1997 | Lutz | |
| 5,628,735 A | 5/1997 | Skow | 604/317 |
| 5,631,057 A | 5/1997 | Sundet | 428/60 |
| 5,728,446 A | 3/1998 | Johnston et al. | 428/167 |
| 5,804,610 A | 9/1998 | Hamer et al. | 522/182 |
| 5,811,035 A | 9/1998 | Mockry | 261/111 |
| 5,815,995 A | 10/1998 | Adam | |
| 5,827,246 A | 10/1998 | Bowen | |
| 5,840,407 A | 11/1998 | Futhey et al. | 428/167 |
| 5,932,298 A | 8/1999 | Moon | 427/496 |
| 6,080,243 A | 6/2000 | Insley et al. | 134/21 |
| 6,290,685 B1 | 9/2001 | Insley et al. | |

* cited by examiner

MICROSTRUCTURED SURFACE FILM ASSEMBLY FOR LIQUID ACQUISITION AND TRANSPORT

BACKGROUND OF THE INVENTION

This invention relates to microstructured films and tapes that have the capability to acquire liquids and to control the directional transport of such liquids for subsequent removal. This transport can be passive or active (i.e., enhanced by an applied potential), and the invention has utility in a number of industrial applications and assemblies.

The collection of liquid in industrial applications (e.g., spills, condensate, ink, pooled fluids, etc.) can cause subsequent problems if the liquid is allowed to remain over a period of time. Some liquid management problems lead to corrosion, power supply loss, excessive weight retention, loss in efficiency, insufficient energy usage, safety hazards, and the like.

Current methods of liquid control focus on the prevention of liquid buildup on a surface through approaches such as absorbent materials, protective films and tapes, and sealants. None of these methods, however, provide for effective liquid removal once liquid is present on a surface.

Transport of liquid across a structured surface may be characterized based upon the mechanism that causes flow of the liquid. Where liquid transport pertains to a non-spontaneous liquid flow regime wherein the liquid flow results, for the most part, from an external force applied to the structured surface, such a liquid transport mechanism is considered "active". On the other hand, where the liquid transport pertains to a spontaneous flow regime wherein the liquid movement results without the introduction of external forces, such a liquid transport mechanism is considered "passive".

Active liquid transport products have been developed based upon specific applications, including absorbent pads or a liquid pervious layer combined with liquid transport devices. For example, mat products including active liquid transport and absorbent pads or liquid pervious layers are described in U.S. Pat. No. 5,437,651 to Todd et al. and U.S. Pat. No. 5,349,965 to McCarver. In each case, channels are defined on a surface of a substrate to direct liquid flow from substantially all of the area of a liquid pervious layer. These products remove liquid while having the liquid pervious layer act as a liquid adsorbing and storing layer and/or to define a liquid receiving layer. In Todd et al., a flexible backing plate is attached to an absorbent portion and a suction source is applied to the backing plate. The backing plate comprises a plurality of channels for directing the vacuum provided by the suction source more evenly across the surface of the absorbent portion. In McCarver, a flexible pad or suction rail having a liquid permeable top surface and a liquid impermeable bottom surface is connected to a vacuum source. The suction draws liquid down into a liquid receiving chamber as it passes through the liquid pervious layer, and draws the accumulated liquid away. The liquid receiving chamber contains separation means dividing the chamber into channels for keeping the chamber from collapsing when the chamber is placed under a negative pressure.

Another flexible liquid transport product is commercially available under the trademark "Fluid Control" floor suction mat, from Technol Medical Products Inc. This product is used to adsorb fluids that fall from a surgical site during a surgical procedure. The device has an absorbent mat that resides above a multitude of parallel and closed channels. Holes are provided in the channel surfaces that interface with the absorbent mat so that fluid recovered by the mat can be drawn into the channels. The parallel channels are connected to a manifold for attachment with suction tubing. Thus, after fluid has accumulated within the mat, removal thereof can be facilitated through the multiple channels by the application of a vacuum.

A fluid guide device having an open structure surface for attachment to a fluid transport source is described in U.S. Pat. No. 6,080,243 to Insley et al. This reference discloses an open structured surface that defines plural channels and a slot for permitting fluid communication between a distribution manifold and at least a plurality of the channels. A fluid transport source, such as a vacuum generator, is connected to the distribution manifold.

Examples of flexible fluid transport devices that utilize both active and passive fluid transport are described in U.S. Pat. No. 3,520,300 to Flower, U.S. Pat. No. 4,747,166 to Kuntz, and U.S. Pat. No. 5,628,735 to Skow. Examples of other channeled mats for fluid removal are shown in U.S. Pat. No. 4,533,352 to Van Beek et al. and U.S. Pat. No. 4,679,590 to Hergenroeder. Examples of passive fluid transport devices having channeled fluid transport structures are described in U.S. Pat. No. 5,514,120. This reference discloses the use of a liquid management member having a microstructure-bearing hydrophilic surface, preferably in combination with a liquid permeable top sheet, a back sheet, and an absorbent core disposed between the top and back sheets. The liquid management member promotes rapid directional spreading of liquids and is in contact with the absorbent core.

SUMMARY OF THE INVENTION

The present invention provides for active and passive transport for liquid acquisition and/or removal in industrial assemblies and applications using microstructured liquid control films.

The liquid control film may be incorporated to transport a liquid to a remote site, to collect a liquid on the film itself, or to disperse the liquid over an increased surface area to promote more rapid evaporation. The microstructured surface has a microstructured topology, and in preferred embodiments is a suitable hydrophilic, polymeric and flexible film. The film properties are described in terms of structure and material.

In one embodiment, the invention is a laminate liquid disposal assembly which includes a liquid control layer and a substrate layer. The liquid control layer has a top side and a bottom side, with the top side having a liquid landing zone for receiving liquid thereon and a liquid removal zone. The top side also has a microstructure-bearing surface with a plurality of channels thereon that facilitate directional flow control of the liquid across the top side from the liquid landing zone to the liquid removal zone. The laminate liquid disposal assembly includes means for attaching the bottom side of the liquid control layer to the substrate layer, and means for removing the liquid from the liquid removal zone on the top side of the liquid control layer.

A porous cap layer may be disposed over the landing zone on the top side of the liquid control layer. Further, the channels on the microstructure-bearing surface have channel ends, and the removing means preferably withdraws the liquid from the channels adjacent one of the channel ends thereof In another embodiment, the removing means withdraws the liquid from the channels adjacent both channel ends thereof. The removing means may include an absorbent material disposed in communication with the liquid removal zone. The removing means may also include a fluid collection manifold in communication with the channels in the liquid removal zone, and the removing means may further include a vacuum generator in fluid communication with the fluid collection manifold. In one embodiment, the removing means includes a liquid drip collector. In a preferred embodiment, the liquid control layer is a polymeric film, which may include a characteristic altering additive or surface coating. That additive may be selected from the group consisting of flame retardants, hydrophobics, hydrophylics, antimicrobial agents, inorganics, metallic particles, glass fibers, fillers, clays and nanoparticles.

In another embodiment, the invention is a laminate floor assembly which includes a liquid control layer and a floor substrate layer. The liquid control layer has a top side and a bottom side, with the top side having a microstructure-bearing surface with a plurality of channels thereon that facilitate directional flow control of a liquid disposed thereon. The laminate floor assembly includes means for attaching the bottom side of the liquid control layer to the floor substrate layer. A cap layer is also provided, with the cap layer having a top side and a bottom side. The bottom side of the cap layer is placed over the top side of the liquid control layer to define a relatively enclosed channel structure therebetween. The laminate floor assembly includes means for moving liquid along the channel structure defined between the top side of the liquid control layer and the bottom side of the cap layer. Preferably, the cap layer comprises a floor covering, and the floor covering may be selected from the group consisting of carpet, tile, linoleum, wood, concrete, metal or fatigue matting. In one embodiment, the cap layer is porous, and may take the form of a nonwoven material. Preferably, the bottom side of the cap layer is affixed to the top side of the liquid control layer by a pressure sensitive adhesive.

In a preferred embodiment, the moving means creates a pressure gradient along the channel structure. Preferably, the top side of the liquid control layer has at least one cross-channel formed therein to facilitate liquid flow between the channels. A liquid removal aperture is then provided through the liquid control layer in communication with the cross-channel and the moving means. In another preferred embodiment, a plurality of cross-channels are formed in the top side of the liquid control layer to facilitate liquid flow between the channels, and the liquid control layer has a plurality of liquid removal apertures therethrough with each liquid removal aperture being in communication with one of the cross-channels and the moving means. In a preferred embodiment, the channels are defined by generally parallel ridges including a first set of ridges having a first height and a second set of ridges having a second, taller height. An upper portion of each ridge of the second set of ridges may have a lower melting temperature than a lower portion thereof Preferably, each channel has channels ends and the moving means withdraws the liquid from the channels adjacent one (or both) of the channel ends. In a preferred embodiment, the liquid control layer is a polymeric film, which may include a characteristic altering additive or surface coating. The additive may be selected from the group consisting of flame retardants, hydrophobics, hydrophylics, antimicrobial agents, inorganics, metallic particles, glass fibers, fillers, clays and nanoparticles. The channels have a pattern geometry selected from the group consisting of linear, curve linear, radial, parallel, nonparallel, random, or intersecting.

One embodiment of the present invention is a method of defining an alternative liquid flow path on a polymeric microstructured liquid transport surface of the type having a plurality of channels which are formed to divert a liquid thereon in a first desired directional path and which are formed to control the displacing and evaporating of the liquid disposed on the surface. The method includes forming at least one cross-channel on the polymeric microstructured liquid transport surface to join at least two adjacent channels of the plurality of channels for liquid flow therebetween.

Preferably, the forming step in the inventive method comprises applying heat and/or pressure to the polymeric microstructured fluid transport surface to define the cross-channel thereon. In a preferred embodiment, the channels on a polymeric microstructured liquid transport surface are defined by generally parallel ridges including a first set of ridges having the first height and a second set of ridges having a second, taller height. Preferably, an upper portion of each ridge of the second set has a lower melting temperature than a lower portion thereof, and the forming step includes applying heat to the polymeric microstructured surface along a linear cross-channel segment thereof, to a temperature high enough to melt the upper portions of the ridges of the second set but not high enough to melt the lower portions thereof Alternatively, the channels are defined by generally parallel ridges with liquid flow valleys therebetween, and the forming step includes cutting away portions of the ridges between adjacent channels. In a preferred embodiment, the polymeric microstructured liquid transport surface defines a top side of a layer having top and bottom opposite sides, and the method of defining an alternative liquid flow path further includes forming a liquid removal aperture through the layer, from top to bottom sides thereof, which is in communication with the cross-channel. The method then can further include urging liquid across the polymeric microstructured liquid transport surface toward the liquid removal aperture, and may yet further include coupling the liquid removal aperture to a liquid collection receptacle. In a preferred embodiment, the inventive method also includes adhering a cap layer (which could be porous) onto the polymeric microstructured liquid transport surface.

In another embodiment of the present invention, the invention is defined as a method for enhancing the rate of evaporation of liquid disposed on a surface which includes defining an exposed face of a film as a polymeric microstructure-bearing surface with a plurality of channels thereon, where the channels are defined by generally spaced apart projections with valleys therebetween. The method includes introducing a liquid onto the polymeric microstructure-bearing surface of the film, wherein the channels are formed to facilitate spontaneous wicking of the liquid along each channel which receives liquid therein so that the exposed evaporative active surface of the liquid is increased by its spatial distribution in the x-direction along the valley of each channel, its spatial distribution in the y-direction between the projections of each channel, as well as by forming meniscus height variations of the liquid in each channel in the z-direction. The method further includes exposing the increased evaporatively active surface area of the liquid on the microstructure-bearing surface to ambient air.

In a preferred embodiment, the inventive method includes exposing the liquid disposed on the microstructure-bearing surface to a moving air stream. Preferably, the inventive method further includes introducing a sufficient quantity of liquid onto the polymeric microstructure-bearing surface to define a continuous flow of liquid over the surface. Further, the inventive method may include collecting non-evaporative liquid that has flowed over the surface, and after further processing of the liquid, recirculating the liquid collected from the surface for reintroduction thereon. In a preferred embodiment, the method includes exposing at least a portion of the liquid flowing over the surface to a moving air stream, which may be moving in the generally opposite direction to the liquid flow direction across the surface. Alternatively, the air stream may be moving in a direction generally perpendicular to the direction that the liquid is flowing across the surface.

In alternate embodiments, the projections are ridges and/or may be discontinuous along the channels. In one embodiment, the polymeric microstructure-bearing surface has first and second ends, and the inventive method includes introducing the sufficient quantity of liquid onto the surface adjacent the first end thereof, and aligning the surface so that its first end is higher than its second end (e.g., the exposed face may be aligned on a generally vertical plane). The inventive method may further include defining additional surface texture features on the polymeric microstructure-bearing surface in order to increase the surface area thereon for supporting the liquid. In one preferred embodiment, the polymeric microstructure-bearing surface has generally parallel channels extending between first and second ends thereof, and the inventive method further includes aligning the surface so that one end of the channels is higher than the other end. Alternatively, the microstructure-bearing surface may be aligned so that an intermediate portion thereof is lower than its first and second ends. In a preferred embodiment, the inventive method further includes providing an additive in the polymeric microstructure-bearing surface, wherein the additive is selected from the group consisting of flame retardants, hydrophobics, hydrophylics, antimicrobial agents, inorganics, metallic particles, glass fibers, fillers, clays and nanoparticles.

BRIEF DESCRIPTION OF THE DRAWINGS

FIG. 12b is a schematic plan view of the test assembly of FIG. 12a.

FIG. 16b is a schematic sectional view as taken along line 16b—16b in FIG. 16a.

FIG. 17b is a schematic sectional view as taken along line 17b—17b in FIG. 17a.

Figure 1A:
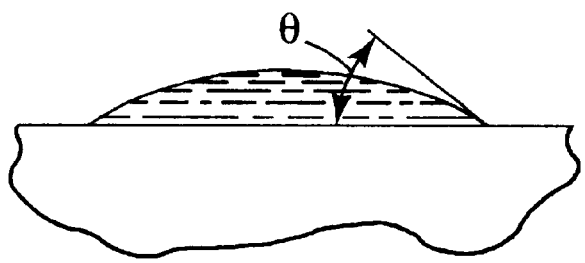
FIGS. 1a and 1b are schematic diagrams used to illustrate interaction of a liquid on a surface.

While several preferred embodiments are set forth in the above drawings, other embodiments are also contemplated, some of which are noted in the following discussion. In all cases, this disclosure presents the illustrated embodiments of the invention as representations, not limitations of the present invention. It is understood that one skilled in the art could devise numerous modifications to the present invention which would still fall within the scope and spirit of the invention.

DEFINITIONS

Unless otherwise specified, the following terms should be construed in accordance with the following definitions:

Fluid control film ("FCF") refers to a film or sheet or layer having at least one major surface comprising a microreplicated pattern capable of manipulating, guiding, containing, spontaneously wicking, transporting, or controlling, a fluid.

Fluid transport film ("FTF") refers to a film or sheet or layer having at least one major surface comprising a microreplicated pattern capable of spontaneously wicking or transporting a fluid.

Fluid transport tape refers to fluid control film with some means for adhering the film to a substrate on its other major surface.

Microreplication means the production of a microstructured surface through a process where the structured surface features retain an individual feature fidelity during manufacture.

Liquid landing zone refers to any area or portion of a structured surface that is aligned for initially receiving liquid thereon.

Liquid removal zone refers to any area or portion of a structured surface that facilitates the transport of liquid over the structured surface and away from the liquid landing zone.

Aspect ratio is the ratio of a channel's length to its hydraulic radius.

Hydraulic radius is the wettable cross-sectional area of a channel divided by the length of its wettable perimeter.

DETAILED DESCRIPTION OF THE PREFERRED EMBODIMENTS

The present invention relates to articles that incorporate a fluid control film component. At the beginning of this section suitable fluid control films will be described generally. Descriptions of illustrative articles incorporating these films, and examples thereof, will follow.

Suitable fluid control films for use in the present invention are described in U.S. Ser. Nos. U.S. Ser. Nos. 08/905,481; 09/099,269; 09/106,506; 09/100,163; 09/099,632; 09/099,555; and 09/099,562; and U.S. Pat. Nos. 5,514,120; 5,728,446; and 6,080,243. Preferred fluid control films of the invention are in the form of sheets or films rather than a mass of fibers. The channels of fluid control films of the invention preferably provide more effective liquid flow than is achieved with webs, foam, or tows formed from fibers. The walls of channels formed in fibers will exhibit relatively random undulations and complex surfaces that interfere with flow of liquid through the channels. In contrast, the channels in the present invention are precisely replicated from a predetermined pattern and form a series of individual open capillary channels that extend along a major surface. These microreplicated channels formed in sheets or films are preferably uniform and regular along substantially each channel length and more preferably from channel to channel. Preferably, such a film or sheet is thin, flexible, cost effective to produce, can be formed to possess desired material properties for its intended application and can have, if desired, an attachment means (such as adhesive) on one side thereof to permit ready application to a variety of surfaces in use. In some embodiments, it is contemplated that the film may be inflexible.

Certain of the fluid control films of the present invention are capable of spontaneously and uniformly transporting liquids along the film channels. Two general factors that influence the ability of fluid control films to spontaneously transport liquids (e.g., water, beverages, condensate, cleaning solutions, etc.) are (i) the geometry or topography of the surface (capillarity, size and shape of the channels) and (ii) the nature of the film surface (e.g., surface energy). To achieve the desired amount of fluid transport capability the designer may adjust the structure or topography of the fluid control film and/or adjust the surface energy of the fluid control film surface. In order for a closed channel wick made from a fluid control film to function it preferably is sufficiently hydrophilic to allow the desired liquid to wet the surface. Generally, to facilitate spontaneous wicking in open channels, the liquid must wet the surface of the fluid control film, and the contact angle be equal or less than 90 degrees minus one-half the notch angle.

The channels of fluid control films of the present invention can be of any geometry that provides desired liquid transport, and preferably one that is readily replicated.

The inventive fluid control films can be formed from any polymeric materials suitable for casting or embossing including, for example, polyolefins, polyesters, polyamides, poly(vinyl chloride), polyether esters, polyimides, polyesteramide, polyacrylates, polyvinylacetate, hydrolyzed derivatives of polyvinylacetate, etc. Polyolefins are preferred, particularly polyethylene or polypropylene, blends and/or copolymers thereof, and copolymers of propylene and/or ethylene with minor proportions of other monomers, such as vinyl acetate or acrylates such as methyl and butylacrylate. Polyolefins are preferred because of their excellent physical properties, ease of processing, and typically lower cost than other thermoplastic materials having similar characteristics. Polyolefins readily replicate the surface of a casting or embossing roll. They are tough, durable and hold their shape well, thus making such films easy to handle after the casting or embossing process. Hydrophilic polyurethanes are also preferred for their physical properties and inherently high surface energy.

Alternatively, fluid control films can be cast from thermosets (curable resin materials) such as polyurethanes, acrylates, epoxies and silicones, and cured by exposure radiation (e.g., thermal, UV or E-beam radiation, etc.) or moisture. These materials may contain various additives including surface energy modifiers (such as surfactants and hydrophilic polymers), plasticizers, antioxidants, pigments, release agents, antistatic agents and the like. Suitable fluid control films also can be manufactured using pressure sensitive adhesive materials. In some cases the channels may be formed using inorganic materials (e.g., glass, ceramics, or metals). Preferably, the fluid control film substantially retains its geometry and surface characteristics upon exposure to liquids.

Generally, the susceptibility of a solid surface to be wet out by a liquid is characterized by the contact angle that the liquid makes with the solid surface after being deposited on the horizontally disposed surface and allowed to stabilize thereon. It is sometimes referred to as the "static equilibrium contact angle", sometimes referred to herein merely as "contact angle".

Figure 1B:
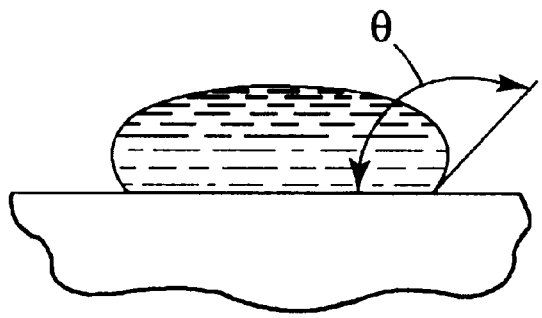

As shown in FIGS. 1a and 1b, the contact angle Theta is the angle between a line tangent to the surface of a bead of liquid on a surface at its point of contact to the surface and the plane of the surface. A bead of liquid whose tangent was perpendicular to the plane of the surface would have a contact angle of 90°. Typically, if the contact angle is 90° or less, as shown in FIG. 1a, the solid surface is considered to be wet by the liquid. Surfaces on which drops of water or aqueous solutions exhibit a contact angle of less than 90° are commonly referred to as "hydrophilic". As used herein, "hydrophilic" is used only to refer to the surface characteristics of a material, i.e., that it is wet by aqueous solutions, and does not express whether or not the material absorbs aqueous solutions. Accordingly, a material may be referred to as hydrophilic whether or not a sheet of the material is impermeable or permeable to aqueous solutions. Thus, hydrophilic films used in fluid control films of the invention may be formed from films prepared from resin materials that are inherently hydrophilic, such as for example, poly(vinyl alcohol). Liquids which yield a contact angle of near zero on a surface are considered to completely wet out the surface. Polyolefins, however, are typically inherently hydrophobic, and the contact angle of a polyolefin film, such as polyethylene or polypropylene, with water is typically greater than 90°, such as shown in FIG. 1b.

Depending on the nature of the microreplicated film material itself, and the nature of the liquid being transported, one may desire to adjust or modify the surface of the film in order to ensure sufficient capillary forces of the article. For example, the surface of the fluid control film may be modified in order to ensure it is sufficiently hydrophilic. Body liquids that will come into contact with the fluid control films of the present invention are aqueous. Thus, if fluid control films of the invention are to be used in applications involving such liquids, those films generally must be modified (e.g., by surface treatment, application of surface coatings or agents), or incorporation of selected agents, such that the film surface is rendered hydrophilic so as to exhibit a contact angle of 90° or less, thereby enhancing the wetting and liquid transport properties of the fluid control film. Suitable methods of making the surface hydrophilic include: (i) incorporation of a surfactant; (ii) incorporation or surface coating with a hydrophilic polymer; and (iii) treatment with a hydrophilic silane. Other methods are also envisioned.

The fluid control films of the invention may have a variety of topographies. Preferred fluid control films are comprised of a plurality of channels with V-shaped or rectangular cross-sections, and combinations of these, as well as structures that have secondary channels, i.e., channels within channels. For spontaneous wicking or transport along open channels, the desired contact angle of the microstructured surface/liquid interface of V-channeled fluid control films is such that:

Theta≦(90°−Alpha/2), wherein Theta is the contact angle of the liquid with the film and Alpha (α) is the average included angle of the secondary V-channel notches. (See, e.g., FIG. 2g).

Any suitable known method may be utilized to achieve a hydrophilic surface on fluid control films of the present invention. Surface treatments may be employed such as topical application of a surfactant, plasma treatment, vacuum deposition, polymerization of hydrophilic monomers, grafting hydrophilic moieties onto the film surface, corona or flame treatment, etc. Alternatively, a surfactant or other suitable agent may be blended with the resin as an internal characteristic altering additive at the time of film extrusion. It is typically preferred to incorporate a surfactant in the polymeric composition from which the fluid control film is made rather than rely upon topical application of a surfactant coating, since topically applied coatings may tend to fill in (i.e., blunt), the notches of the channels, thereby interfering with the desired liquid flow to which the invention is directed. When a coating is applied, it is preferably thin to facilitate a uniform thin layer on the structured surface. An illustrative example of a surfactant that can be incorporated in polyethylene fluid control films is TRITON™ X-100 (available from Union Carbide Corp., Danbury, Conn.), an octylphenoxypolyethoxyethanol nonionic surfactant, e.g., used at between about 0.1 and 0.5 weight percent. An illustrative method for surface modification of the films of the present invention is the topical application of a 1 percent aqueous solution of the reaction product comprising 90 weight percent or more of:

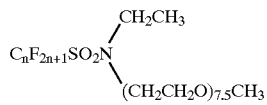

Formula 1
wherein n=8 (97 percent), n=7 (3 percent), and 10 weight percent or less of:

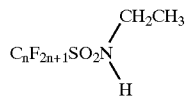

Formula 2
wherein n=8 (97 percent), n=7 (3 percent). Preparation of such agents is disclosed in U.S. Pat. No. 2,915,554 (Ahlbrecht et al.).

Other surfactant materials that are suitable for increased durability requirements for industrial applications of the present invention include Polystep® B22 (available from Stepan Company, Northfield, Ill.) and TRITON™ X-35 (available from Union Carbide Corp., Danbury, Conn.).

As discussed above, a surfactant or mixture of surfactants may be applied to the surface of the fluid control film or impregnated into the article in order to adjust the properties of the fluid control film or article. For example, it may be desired to make the surface of the fluid control film more hydrophilic than the film would be without such a component.

Preferred embodiments of the present invention retain the desired fluid transport properties throughout the life of the product into which the fluid control film is incorporated. In order to ensure the surfactant is available throughout the life of the fluid control film the surfactant preferably is available in sufficient quantity in the article throughout the life of the article or is immobilized at the surface of the fluid control film. For example, a hydroxyl functional surfactant can be immobilized to a fluid control film by functionalizing the surfactant with a di- or tri-alkoxy silane functional group. The surfactant could then be applied to the surface of the fluid control film or impregnated into the article with the article subsequently exposed to moisture. The moisture would result in hydrolysis and subsequent condensation to a polysiloxane. Hydroxy functional surfactants, (especially 1,2 diol surfactants), may also be immobilized by association with borate ion. Suitable surfactants include anionic, cationic, and non-ionic surfactants, however, nonionic surfactants may be preferred due to their relatively low irritation potential. Polyethoxylated and polyglucoside surfactants are particularly preferred including polyethoxylated alkyl, aralkyl, and alkenyl alcohols, ethylene oxide and propylene oxide copolymers such as "Pluronic" and "Tetronic", alkylpolyglucosides, polyglyceryl esters, and the like. Other suitable surfactants are disclosed in Ser. No. 08/576,255.

As discussed above, a surfactant such as a hydrophilic polymer or mixture of polymers may be applied to the surface of the fluid control film or impregnated into the article in order to adjust the properties of the fluid control film or article. Alternatively, a hydrophilic monomer may be added to the article and polymerized in situ to form an interpenetrating polymer network. For example, a hydrophilic acrylate and initiator could be added and polymerized by heat or actinic radiation.

Suitable hydrophilic polymers include: homo and copolymers of ethylene oxide; hydrophilic polymers incorporating vinyl unsaturated monomers such as vinylpyrrolidone, carboxylic acid, sulfonic acid, or phosphonic acid functional acrylates such as acrylic acid, hydroxy functional acrylates such as hydroxyethylacrylate, vinyl acetate and its hydrolyzed derivatives (e.g. polyvinylalcohol), acrylamides, polyethoxylated acrylates, and the like; hydrophilic modified celluloses, as well as polysaccharides such as starch and modified starches, dextran, and the like.

As discussed above, a hydrophilic silane or mixture of silanes may be applied to the surface of the fluid control film or impregnated into the article in order to adjust the properties of the fluid control film or article. Suitable silane include the anionic silanes disclosed in U.S. Pat. No. 5,585,186, as well as non-ionic or cationic hydrophilic silanes. Cationic silanes may be preferred in certain situations and have the advantage that certain of these silanes are also believed to have antimicrobial properties.

As previously mentioned, the channels of fluid control films of the present invention can be of any geometry that provides desired liquid transport. In some embodiments, the fluid control film will have primary channels on only one major surface as shown in FIGS. 2a–2i. In other embodiments, however, the fluid control film will have primary channels on both major surfaces, as shown in FIGS. 2j and 2k.

Figure 2A:
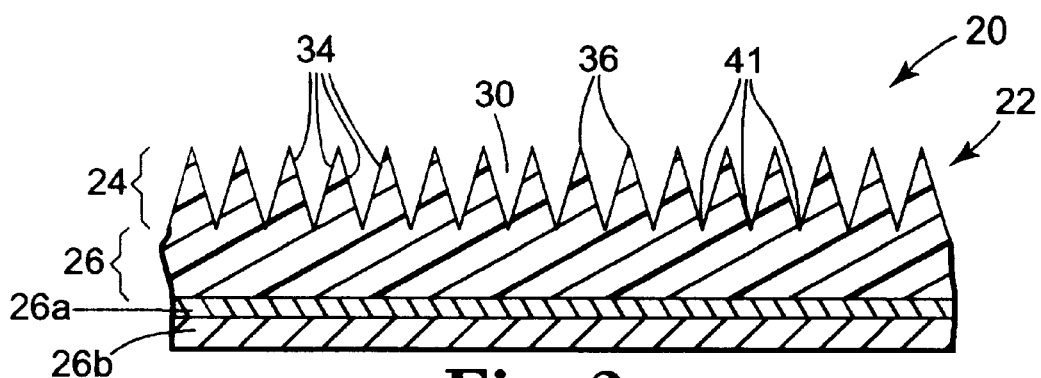
FIGS. 2a through 2k are cross-sectional cutaway views of illustrative embodiments of fluid control films of the present invention.

As shown in FIG. 2a, a fluid control film 20 of the present invention includes a layer 22 of polymeric material that has a structured surface 24 on one of its two major surfaces. The layer 22 includes a body layer 26 from which the structured surface 24 projects. The body layer 26 serves to support the structured surface 24 in order to retain the individual structured features together in layer 22.

As shown in FIG. 2a, channels 30 can be defined within the layer 22 in accordance with the illustrated embodiment by a series of v-shaped sidewalls 34 and peaks 36. Each peak or projection may define a continuous ridge running along each channel, or the peaks may be formed as discontinuous elements (e.g., pins, bars, etc.) which still functionally serve to define the channels therebetween. In some embodiments, a cap layer (not shown in FIG. 2a) is provided over the structured surface 24 to aid in channel definition. In some cases, the sidewalls 34 and peaks 36 may extend entirely from one edge of the layer 22 to another without alteration— although, in some applications, it may be desirable to shorten the sidewalls 34 and thus extend the peaks 36 only along a portion of the structured surface 24. That is, channels 30 that are defined between peaks 36 may extend entirely from one edge to another edge of the layer 22, or such channels 30 may only be defined to extend over a portion of the layer 22. Channels 30 that extend only over a portion may begin at an edge of the layer 22, or they may begin and end intermediately within the structured surface 24 of the layer 22. The channels 30 are defined in a predetermined, preferably ordered arrangement over a continuous surface of polymeric material.

Figure 2B:
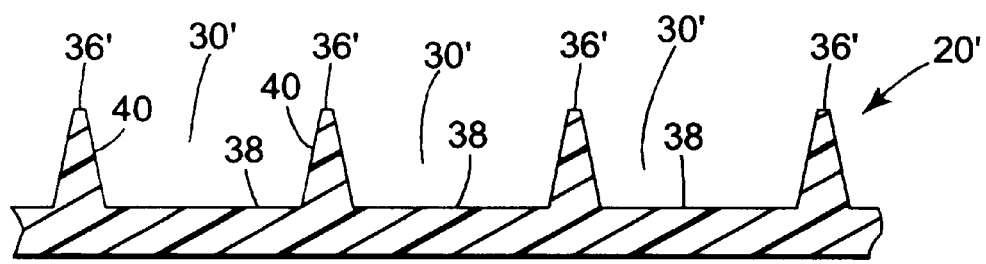

Other channel configurations are contemplated. For example, as shown in FIG. 2b, a fluid control film 20' has channels 30' which have a wider flat valley between slightly flattened peaks 36'. Like the FIG. 2a embodiment, a cap layer (not shown) can be secured along one or more of the peaks 36' to define discrete channels 30'. In this case, bottom surfaces 38 extend between channel sidewalls 40, whereas in the FIG. 2a embodiment, sidewalls 34 connect together along lines 41.

Figure 2C:
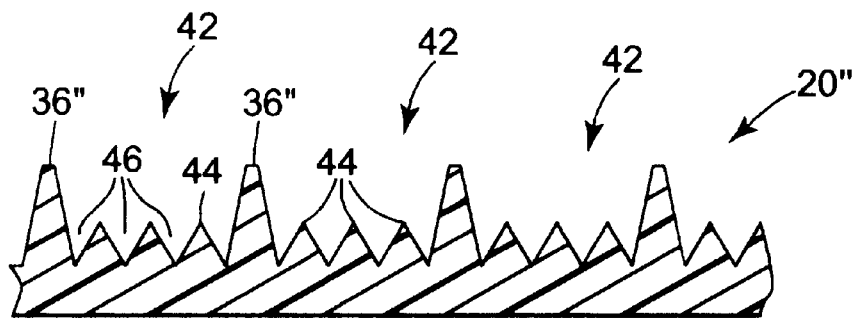
Figure 2D:
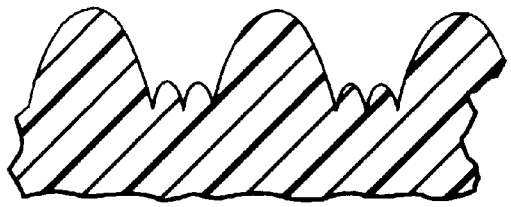
Figure 2E:
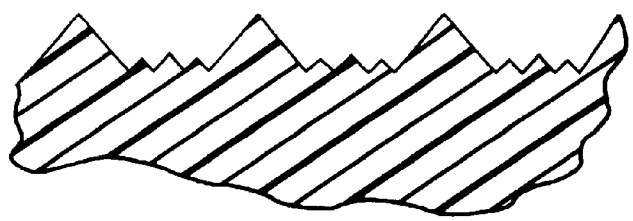
Figure 2F:

FIG. 2c illustrates an alternate fluid control film 20" where wide channels 42 are defined between peaks 36", but instead of providing a flat surface between channel sidewalls 40, a plurality of smaller peaks 44 are located between the sidewalls 40' of the peaks 36". These smaller peaks 44 thus define secondary channels 46 therebetween. Peaks 44 may or may not rise to the same level as peaks 36", and as illustrated create a first wide channel 42 including smaller channels 46 distributed therein. The peaks 36" and 44 need not be evenly distributed with respect to themselves or each other.

FIGS. 2d–2k illustrate various alternative embodiments of the fluid control film of the present invention. Although FIGS. 2a–2k illustrate elongated, linearly-configured channels, the channels may be provided in other configurations. For example, the channels could have varying cross-sectional widths along the channel length—that is, the channels could diverge and/or converge along the length of the channel. The channel sidewalls could also be contoured rather than being straight in the direction of extension of the channel, or in the channel height. Generally, any channel configuration that can provide at least multiple discrete channel portions that extend from a first point to a second point within the fluid transport device are contemplated. The channels may be configured to remain discrete along their whole length if desired.

Figure 2G:
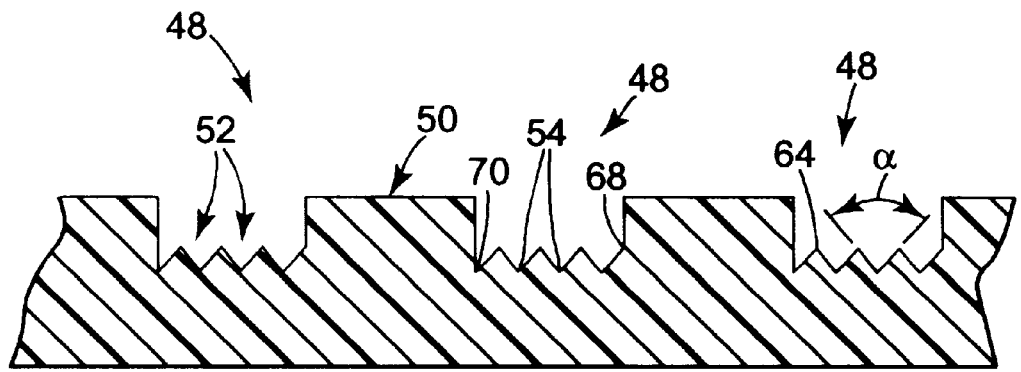
Figure 2H:
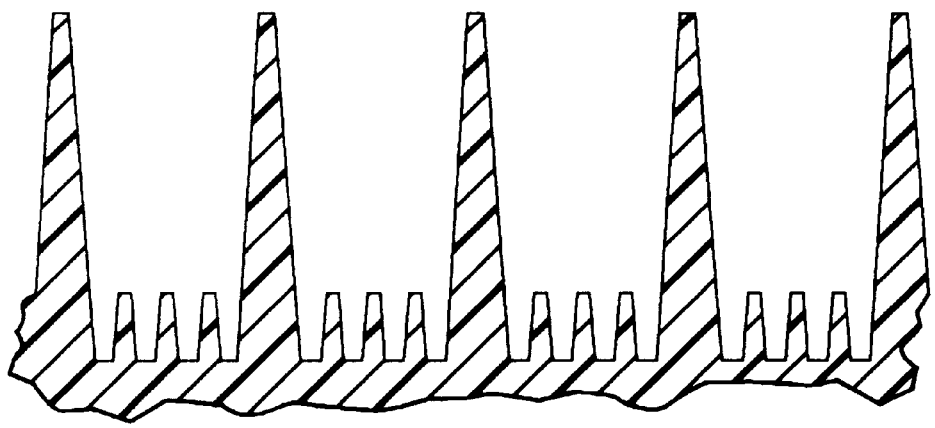

With reference to FIG. 2g, one preferred geometry is a rectilinear primary channel 48 in a flat film 50. The primary channel 48 has included secondary channels 52 which forms a multitude of notches 54. The notches 54 (or secondary channels 52, where the secondary channels 52 are V-shaped and have substantially straight sidewalls) have a notch included angle of (i.e., angle Alpha) from about 10° to about 120°, preferably from about 10° to about 100°, and most preferably from about 20° to about 95°. The notch included angle is generally the secant angle taken from the notch to a point 2 to 1000 microns from the notch on the sidewalls forming the notch, preferably the notch included angle is the secant angle taken at a point halfway up the secondary channel sidewalls. It has been observed that notches with narrower included angular widths generally provide greater vertical wicking distance. However, if Alpha is too narrow, the flow rate will become significantly lower. If Alpha is too wide, the notch or secondary channel may fail to provide desired wicking action. As Alpha gets narrower, the contact angle of the liquid need not be as low, to get similar liquid transport, as the contact angle must be for notches or channels with higher angular widths.

The primary channel included angle is not critical except in that it should not be so wide that the primary channel is ineffective in channeling liquid. Generally, the primary channel maximum width is less than 3000 microns and preferably less than 1500 microns. The included angle of a V-channel shaped primary channel will generally be from about 10 degrees to 120 degrees, preferably 30 to 110 degrees. If the included angle of the primary V-channel is too narrow, the primary channel may not have sufficient width at its base so that it is capable of accommodating an adequate number of secondary channels. Generally, it is preferred that the included angle of the primary channel be greater than the included angle of the secondary channels so as to accommodate the two or more secondary channels at the base of the primary channel. Generally, the secondary channels have an included angle at least 20 percent smaller than the included angle of the primary channel (for V-shaped primary channels).

With reference to FIGS. 2g and 2j, the depth of the primary channels (48, 56) (the height of the peaks or tops above the lowermost channel notch), "d", is substantially uniform. Preferably, the height "d" ranges from about 5 to about 3000 microns, more preferably from about 25 to about 1500 microns, even more preferably from about 50 to about 1000 microns, and most preferably from about 50 to about 350 microns. It will be understood that in some embodiments films with channels (48, 56) having depths larger than the indicated ranges may be used. If the channels are unduly deep, the overall thickness of the fluid control film will be unnecessarily high and the film may tend to be stiffer than is desired. The width of the primary channel at its base may be sufficient to accommodate two or more secondary channels.

FIGS. 2j and 2k illustrate fluid control films having primary channels on both major surfaces. As shown in FIG. 2j, the primary channels 56 may be laterally offset from one surface to the other surface or may be aligned directly opposite each other as shown in FIG. 2k. A fluid control film with offset channels as shown in FIG. 2j provides a maximum amount of surface area for wicking while at the same time using a minimum amount of material. In addition, a fluid control film with offset channels can be made so as to feel softer, due to the reduced thickness and boardiness of the sheet, than a fluid control film with aligned channels as shown in FIG. 2k. As shown in FIG. 2k, fluid control film of the invention may have one or more holes or apertures 58 therein, which enable a portion of the liquid in contact with the front surface of the fluid control film to be transported to the back surface of the film, to improve liquid control. The apertures need not be aligned with the notch of a channel and do not need to be of about equal width as the channels. The surfaces of the fluid control film within the apertures is preferably hydrophilic.

As illustrated in FIGS. 2g and 2j, in each primary channel (48, 56) are at least two secondary channels (52, 60) and at least two notches (54, 62), the notch or notches of each secondary channel (52, 60) is separated by a secondary peak (64, 66). Generally, each secondary channel will generally have only one notch, but a secondary channel will have two notches if the secondary channel is rectangular. The secondary peak (64, 66) for V-channel shaped secondary channels is generally characterized by an included angle β which is generally equal to $(\alpha^1+\alpha^2)/2$ where $\alpha^1$ and $\alpha^2$ are the included angles of the two adjacent V-channel shaped secondary channels (52, 60), assuming that the two sidewalls forming each secondary channel are symmetrical and not curved. Generally, the angle β would be from about 10° to about 120°, preferably from about 10° to about 110°, and most preferably from about 20° to about 100°. The secondary peak could also be flat (in which case the included angle would theoretically be 0°) or even curved, e.g., convex or concave, with no distinct top or included angle.

Preferably, there are at least three secondary channels (52, 60) and/or at least three notches for each primary channel (48, 56), (including any notches (54, 62) associated with the end channels such as notches 68 or 70 as shown in FIG. 2g).

The depth of one of the secondary channels (52, 60) (the height of the top of the secondary peaks 64 over the notches 54) is uniform over the length of the fluid control films, and is typically at least 5 microns. The depth of the secondary channels (52, 60) is generally 0.5 to 80 percent of the depth of the primary channels, preferably 5 to 50 percent. The spacing of the notches (54, 62) on either side of a peak is also preferably uniform over the length of the fluid control film. Preferably the primary and/or secondary channel depth and width varies by less than 20 percent, preferably less than 10 percent for each channel over a given length of the fluid control film. Variation in the secondary channel depth and shape above this range has a substantial adverse impact on the rate and uniformity of liquid transport along the fluid control film. Generally the primary and secondary channels are continuous and undisturbed.

Figure 3A:
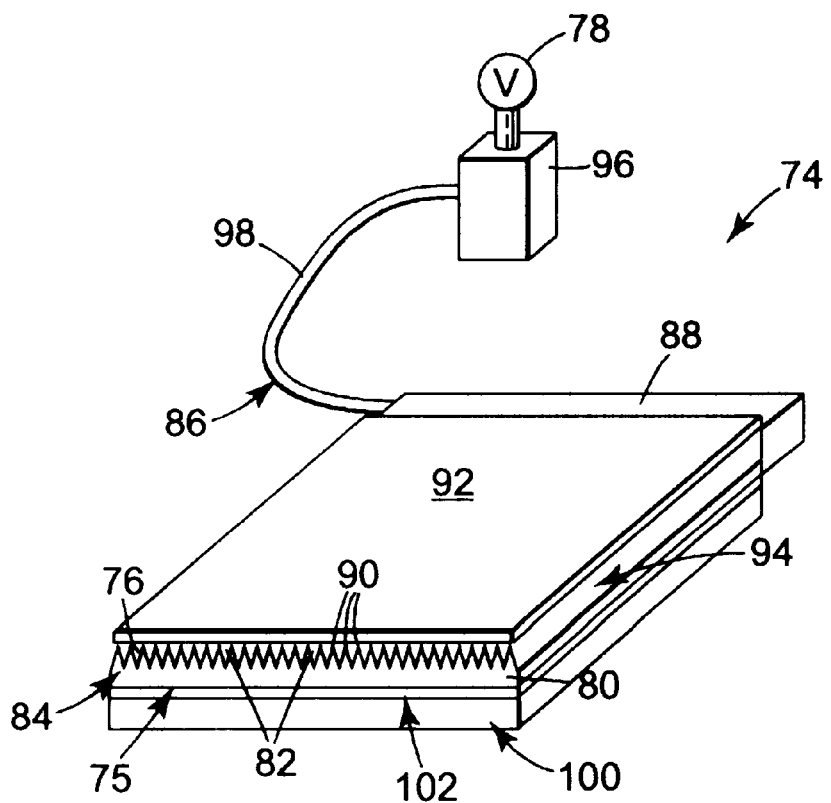
FIG. 3a is a perspective view of an active fluid transport device in accordance with the present invention which has a structured layer, a cap layer mounted over the structured layer to provide multiple discrete channels that are in communication with a vacuum source, and an adhesive layer bonding the structured layer to a substrate.

In FIG. 3a an active fluid transport device 74 is illustrated which includes a layer 75 of polymeric material that has a structured surface 76 on one of its two major surfaces. The device 74 also includes a source 78 for providing a potential to assist in moving a liquid over the structured surface 76 of the active fluid transport device 74. Layer 75 also includes a body layer 80 from which the structured surface 76 projects. Body layer 80 serves to support structured surface 76 to retain the individual structured features together in layer 75, and may include additives or additional layers as described herein.

Layer 75 may be comprised of flexible, semi-rigid, or rigid material, which may be chosen depending on the particular application of the active fluid transport device 74. The layer 75 comprises a polymeric material because such materials can be accurately formed to create a microstructured surface 76. Substantial versatility is available because polymeric materials possess many different properties suitable for various needs. Polymeric materials may be chosen, for example, based on flexibility, rigidity, permeability, etc. The use of a polymeric layer 75 also allows a structured surface to be consistently manufactured to produce a large number of high density of channels, that when capped, form discrete liquid flow channels 82. Thus, a highly distributed liquid transport system (i.e., one that has many channels that distribute the potential along the face of the structured surface) can be provided that is amenable to being manufactured at a high level of accuracy and economy. The structured polymeric surface 76 may be made from the same or different materials of the body layer 75.

As shown in FIG. 3a, each of the channels 82 is opened at one edge of the layer 75 to define channel inlets 84. Liquid can thus pass through the inlets 84 guided by the channels 82 toward a further edge of the layer 75 to a connector 86. The connector 86 preferably is in fluid communication with each of the channels 82 through outlets (not shown) and also is in liquid communication with the potential source 78. The connector 86 may be fashioned in a variety of forms but as illustrated in FIG. 3a, it includes a manifold 88. Manifold 88 is provided with a plenum (not shown) that is defined internally therein and which is in fluid communication with channels 82. The plenum may simply comprise a chamber within the manifold 88 that is sealingly connected to at least a plurality of the channels 82. The manifold 88 may be flexible, semi-rigid, or rigid, like the layer 75. A second manifold (not shown) also may be provided at the side of layer 75 having inlets 84 so as to supply liquid to the channels 82, depending on the particular application. The manifolds may be formed using microreplicated channels (e.g., converging channels).

In accordance with the invention, the connector may take on essentially any adaptation that enables the potential to be transferred from the source to the multiple channels. Although a manifold with a plenum and a tubing have been described, other connectors—such as compression couplings, or seals and gaskets that fluidically join a conduit to the flow channels and permit the isolation or partition of regions of higher and lower potential from the surrounding environment—are contemplated for use in this invention. The connector could also include capillary fibers, for example, less than 10 μm in inner diameter, each in fluid communication with an individual channel to allow individual liquids to flow discretely through separate channels. The connector could also be one or more molded chambers, a microstructured fluid conduit integrally or nonintegrally disposed relative to the discrete flow channels, or for example, a system or mechanism that allows the discrete microstructured flow channels to be seated in a centrifuge or that allows a flow stream such as a jet to be directed at channel inlets or outlets.

To close off or enclose at least part of the channels 82 along peaks 90 thereof, a cap layer 92 may be juxtaposed against the structured surface 76. Cap layer 92 thus closes at least a plurality of the channels 82 to create discrete liquid flow channels in a capillary module 94. The capillary module 94 typically would have a thickness of 1 to 10 millimeters (mm), and more typically 2 to 6 mm. Cap layer 92 may likewise sealingly connect to the manifold 88 so that plural discrete channels 82 provide active liquid transport channels based upon the creation of a potential difference along the channels 82 from a first potential to a second potential. Cap layer 92 typically has a thickness of about 0.01 to 2 mm, and could be comprised of any protective film, flooring laminate, or other functional part of an industrial device. If the channels of the invention are hermetically sealed then the flexible system of channels could generally withstand high pressure without rupture, as a result of the hoop strength of the small individual channels.

The cap layer 92 may be bonded to the peaks 90 of some or all of the structured surface 76 to enhance creation of discrete channels 82. This can be done thermally or by using conventional adhesives that are compatible with the cap layer material 92 and the polymeric structured layer 75 (when an adhesive is used for this purpose, it must be selected so that it does not immediately, or over time, flow into and close off the channels 82 to which it is adhered). The formation of discrete channels 82 may be accomplished through heat bonding, ultrasonic welding, compression, or mechanical engagement such as an interference fit. Bonds may be provided entirely along the peaks 90 to the cap layer 92, or the bonds may be spot welds or bonds that may be placed thereon in an ordered or random pattern. Alternatively, the cap layer 92 may simply be placed over the structured surface 76, without an adhesive or bond therebetween.

Cap layer 92 may be made from a polymeric material such as the polymers described herein for the structured polymeric layer. Optionally, cap layer 724 may be a material such as a spunlaced, spunbond, blown microfiber or carded nonwoven. Polymers may be chosen such that the cap layer 92 can be secured to the structured surface 76 without using an adhesive. Such a polymer could be chosen such that the cap layer becomes securely welded to the structured surface by applying heat, for example, as from an ultrasonic welding operation. In some applications, the cap layer may be formed from more than one layer (e.g., an initial nonwoven layer covered by a linoleum layer). In this situation, the nonwoven layer may act as a debris filter above the structured surface, and may also serve to increase the effective surface presented for laying down or adhering the linoleum layer.

The potential source may comprise essentially any means capable of establishing a potential difference along a plurality of the flow channels 82 to encourage liquid movement from a first location to a second location. The potential is sufficient to cause, or assist in causing, liquid flow through a plurality of flow channels 82, which is based in part on the fluid characteristics of any particular application. As shown in FIG. 3a, the potential source 78 may comprise a vacuum generator (V) that is conventionally or otherwise connected to an optional collector receptacle 96. The collector receptacle 96 is fluidically connected to the manifold 88 by way of a conventional flexible tube 98. Thus, liquid can be drawn from outside the capillary module 94 into the inlets 84, through channels 82, through manifold 88, through tube 98, and into the collection receptacle 96. The receptacle 96 may advantageously be operable to empty its contents or may be otherwise connected to conventional drainage systems.

In the case where the potential source 78 comprises a vacuum generator (V), the vacuum provided to the channels 82 via manifold 88 can be sufficient to adequately seal the cap layer 92 to the peaks 90. That is, the vacuum itself will hold the cap layer 92 against peaks 90 to form discrete channels 82. Preferably, each of the channels 82 that are defined by the structured surface 76 is closed off by the cap layer 92 so as to define a maximum number of discrete channels 82 capable of independently accommodating the potential. Liquid crossover between channels 82 may be effectively minimized, and the potential provided from an external source can be more effectively and efficiently distributed over the structured surface 76 of layer 75. When the potential source 78 comprises a vacuum generator, manifold 88 need not be sealed to channels 82 but may be simply placed adjacent an open section of channels 82.

Connection between a microstructure-bearing surface, or capillary module, to a fluid conveyance or potential source can be achieved through a detachable or affixed manifold or manifolds as required. Multiple potential sources may also be employed depending on the particular adaptation or application. Pressure differential is an efficient liquid flow motivation method or potential that may be used to drive flow across a microstructure-bearing surface. Pressure differential can be established readily through use of a pumping system and applied either in the form of positive or negative pressure.

Other potential sources 78 may be used in the present invention instead of or in conjunction with a vacuum generation device (V). Essentially any manner of causing or encouraging liquid flow through the channels 82, is contemplated for using this invention. The potential source is separate from the channeled structure and/or capillary module, or in other words is not intrinsic to the channeled structure and/or capillary module. That is, the invention does not rely solely on the properties of the channeled structure to cause liquid movement, for example, by capillary action. Examples of other potential sources include but are not limited to, vacuum pumps, vacuum aspirators, pressure pumps and pressure systems such as a fan, magneto hydrodynamic drives, magnetic systems, acoustic flow systems, centrifugal spinning, hydrostatic heads, gravity, absorbents, and any other known or later developed fluid drive system utilizing the creation of a potential difference that causes or encourages liquid flow to at least to some degree. Additionally, any applied field force that acts directly on the liquid such as a centrifugal force or magnetic field that causes liquid to move within the channels of the invention may be considered a liquid motive potential. In addition, the potential source may operate to move liquid onto the structured surface rather than remove liquid off of or away from the structured surface. Liquid may also be caused to flow through channels by the action of a siphon where atmospheric pressure creates the potential to move liquid in the channels. In an application of the present invention in an aircraft, the pressurization of the aircraft may be employed to achieve the pressure differential required to define a potential for liquid flow.

Figure 3B:
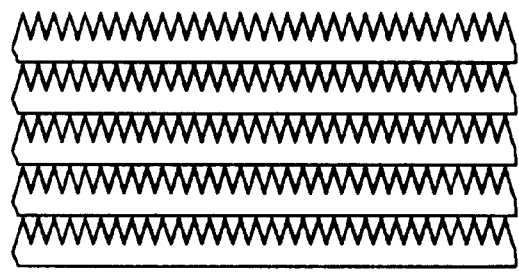
FIG. 3b illustrates, in partial sectional view, a stacked arrangement of structured layers made according to the present invention.

Although the liquid transport device shown in FIG. 3a has a structured surface 76 comprising multiple V-shaped peaks 90 (e.g., as shown in FIG. 2a), other topography configurations for the structured surface 76 are contemplated. In addition, in some embodiments, two or more structured surfaces may be overlaid to increase flow capacity (see, e.g., FIG. 3b). Such an arrangement likewise multiplies the possible configurations for relative channel orientation among the stacked layers of structured surfaces, as well as the possible arrangements for application of a potential to one or more of the layers. The stacked layers may comprise different channel configurations and/or numbers of channels, depending on a particular application. Furthermore, this type of stacked construction can be particularly suitable for applications that are restricted in width and therefore require a relatively narrow fluid transport device from which a certain fluid transfer capacity is desired. Thus, a narrow device can be made having increased flow capacity. The layers in the stack may be bonded to one another in any number of conventional ways as described herein, or they may simply be stacked upon one another such that the structural integrity of the stack can adequately define discrete flow channels. This ability may be enhanced, as described above, when a vacuum is utilized as the potential source. The stack could include multiple connectors to allow multiple potential sources of varying potential to be attached to as subsets in the stack.

As seen in FIG. 3a, the layer 75 is mounted to a substrate 100 by suitable adhesive means 102 therebetween. The adhesive means 102 is preferably a pressure sensitive adhesive, but may comprise other fastening arrangements, such as opposed two part mechanical fasteners, other adhesive compositions or tapes, hook and loop fasteners, and opposed fields such as electrical or magnetic. The adhesive layer means 102 may simply be a layer of pressure sensitive adhesive which is continuous or discontinuous, or the adhesive thereon may be formed to have a microstructured surface as defined herein. In one embodiment, the adhesive may be formed to itself include the layer 75 and structured surface 76 thereon.

The substrate 100 may assume any form suitable for support of the layer 75, and may be formed from a rigid material or a flexible material. For example, the substrate may be metal, wood or formed from a polymer material, and may serve as a portion of a floor, wall or an exterior or interior machine or structure surface. Depending upon the desired application, the fluid transport device 74 may include a cap layer 92 and/or connector 86 for collecting liquid.

Figure 4:
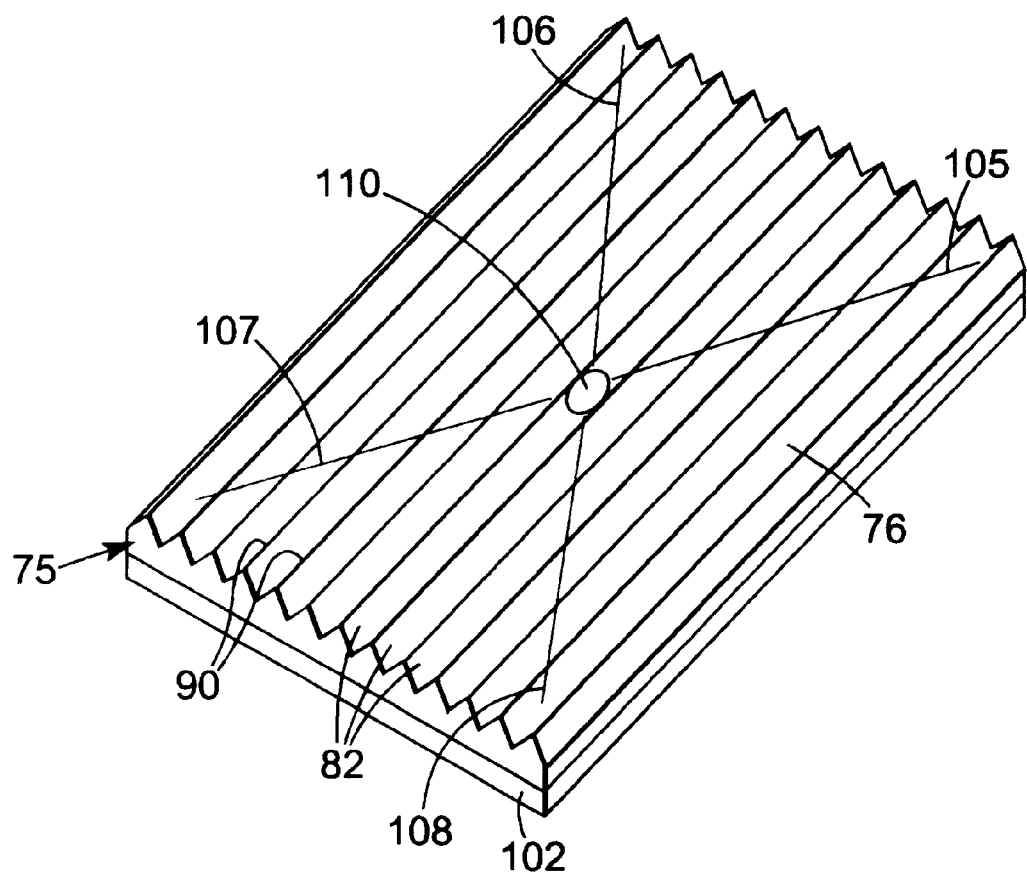
FIG. 4 is a prospective view of an alternative active fluid transport device in accordance with the present invention.

In some applications, an alternative form of a liquid collection system is desired. FIG. 4 illustrates one such system. The layer 75 has the structured surface 76 on its top side and adhesive means 102 on its bottom side. The structured surface 76 has a plurality of channels 82 therein (shown as parallel linear channels in FIG. 4). One or more cross-channels are formed in the structured surface 76, such as cross-channels 105, 106, 107 and 108. The cross-channels are added to the structured surface 76 after its initial formation (e.g., after the structured surface 76 has been molded into the layer 75 of polymeric material). Each cross-channel may be formed by removing portions of the peaks 90 between adjacent channels 82, such as by cutting those portions away or removing them by the application of heat and/or pressure, or by overlaying a strip of material capable of transporting liquid therethrough on top of the structured surface 76.

A post embossing method (after the microstructured layer 75 has been applied to the substrate) achieves a preferred embodiment for liquid communication along the channels on the face of the fluid transport device 75. The structured surface 76 may be embossed with a hot wire to define each cross-channel in order to provide a means for liquid communication between the channels 82 to existing or newly defined liquid outlets in application. Such a liquid outlet may include a central liquid removal aperture 110 (as seen in FIG. 4) or, in the case where the cross-channels do not intersect, a separate liquid removal aperture for each cross-channel. Each liquid removal aperture extends through the layer 75, adhesive 102 and the substrate 100.

Figure 5:
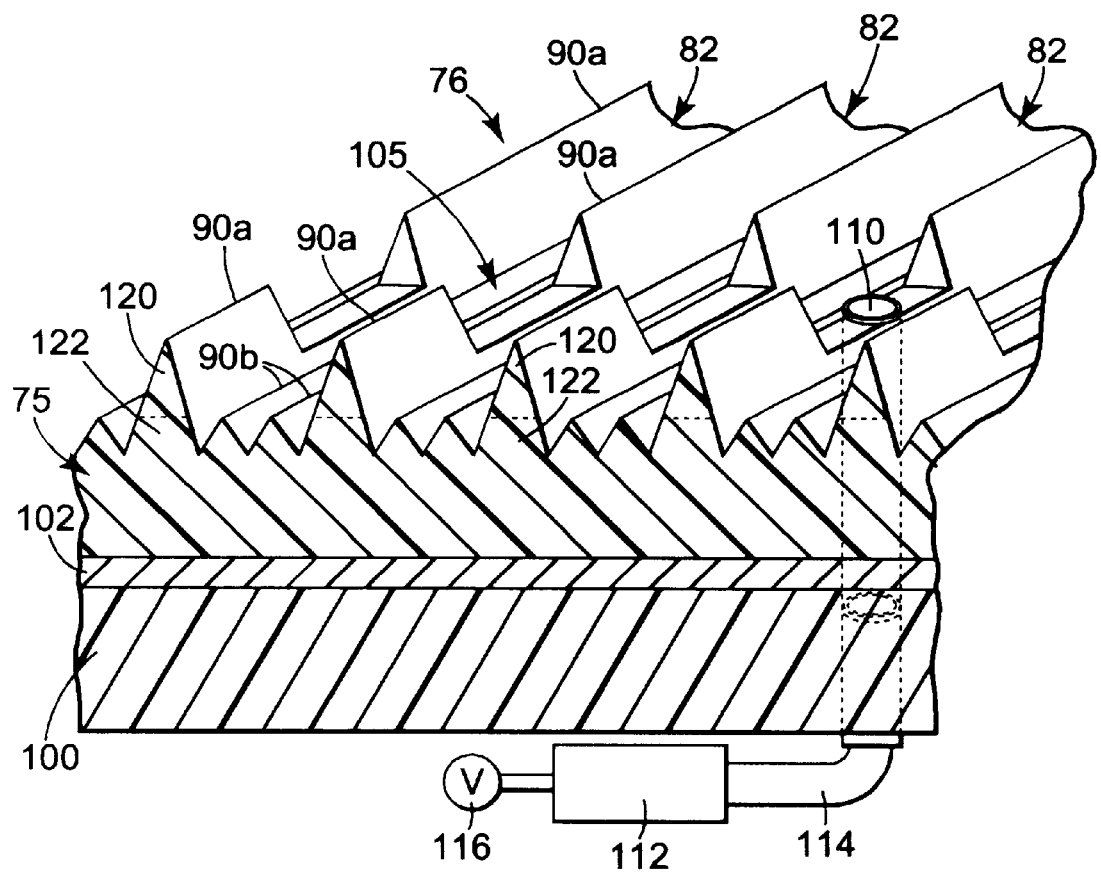
FIG. 5 is a greatly enlarged sectional view of a portion of the active fluid transport device of FIG. 4.

As illustrated in FIG. 5, a liquid collection system may be fluidly coupled to the aperture 110. In some applications, the liquid collector may include a reservoir 112 for liquid, coupled to the aperture 110 by a suitable conduit 114. Further, the system may include a source 116 for providing a potential to the system for moving liquid over the structured surface 76 (through channels 82, cross-channels 105, 106, 107 or 108, aperture 110, conduit 114 to the reservoir 112). The reservoir 112 may simply be a collector site or sump, and the source 116 (if employed) may be a vacuum pump or any of the other types described herein. In applications where multiple apertures 110 are provided (e.g., one aperture for each cross-channel), multiple conduits 114 may likewise be provided, with each conduit 114 connecting one or more of the apertures 110 to the reservoir 112 (or to separate reservoirs).

As also seen in FIG. 5, the structured surface 76 may take a form similar to that illustrated in FIG. 2c, wherein some channel peaks 90a are higher than other channel peaks 90b. Thus, when removing peak material to define a cross-channel (such as cross-channel 105 in FIG. 5), only an upper portion 120 of each peak 90a need be removed in order to define the cross-channel and define a means for controlled liquid flow across the channels 82 of the structured surface 76. In one preferred embodiment, the upper portion 120 of each higher peak 90a is formed from a material having a lower melting temperature than a lower portion 122 of the peak 90a, and the cross-channel is formed by applying heat to a temperature high enough to melt the upper portion 120 of the peak 90a, but not melt its lower portion 122. While a cap layer would typically be employed in the active fluid transport device illustrated in FIGS. 4 and 5, the cap layer has been not shown in those figures for purposes of illustration.

Figure 6A:
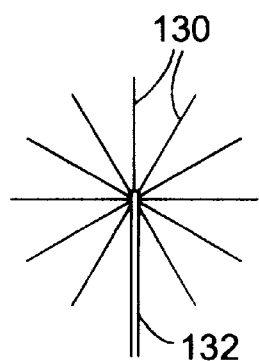
FIGS. 6a and 6b are plan views of structured layers illustrating alternative channel structures that may be used in an active fluid transport device in accordance with the present invention.
Figure 6B:
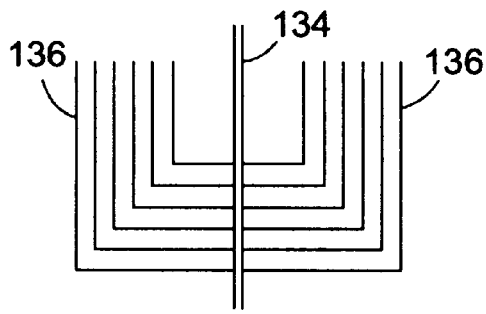

While parallel channels (e.g., FIG. 5) may be preferred, alternate channel patterns are contemplated, as mentioned above. FIGS. 6a and 6b schematically illustrate alternate channel configurations in plan views that may define a structured surface in a fluid transport device of the present invention. As shown in FIG. 6a, the structured surface may have multiple discrete non-parallel converging channels 130 to provide for intermediate collection of liquid. These converging channels 130 connect to a single discrete channel 132 which may, in turn, be connected to an outlet port or liquid removal aperture (not shown). As shown in FIG. 6b, a central channel 134 connects to a plurality of channel branches 136 that may be designed to cover a particular area for similar reasons. Again, generally any channel pattern is contemplated in accordance with the present invention as long as a plurality of discrete channels are provided over a portion of the structured surface from a first point to a second point. Like the above embodiments, the patterned channels shown in FIGS. 6a and 6b are preferably covered with a cap layer for further defining discrete flow channels that allow the potential to be accommodated along a particular channel essentially independent of its neighboring channels.

As to any of the channels contemplated above and in accordance with the present invention, such channels are defined within a structured layer by the structured surface of a first major surface of the layer. The channels in accordance with the present invention are configured to be discrete to allow any one channel to receive liquid from the ambient environment independently of the other channels. The microstructured size of each channel encourages single-phase flow of liquid in bulk volumes. Without having air entrained in the liquid, noise generation is significantly reduced and less stress can be placed on liquids that are transported through the active fluid transport device.

The individual flow channels of the microstructured surfaces of the invention are substantially discrete. That is, liquid can move through the channels independent of liquid in adjacent channels. The channels independently accommodate the potential relative to one another to direct a liquid along or through a particular channel independent of adjacent channels. Preferably, liquid that enters one flow channel does not, to any significant degree, enter an adjacent channel, although there may be some diffusion between adjacent channels. It is important to effectively maintain the discreteness of the micro-channels in order to effectively transport the liquid and maintain advantages that such channels provide. Not all of the channels, however, may need to be discrete for all embodiments. Some channels may be discrete while others are not. Additionally, channel "discreteness" may be a temporary phenomenon driven, for example, by fluctuating pressures.

The structured surface is a microstructured surface that defines discrete flow channels with each channel having a minimum aspect ratio (length/hydraulic radius) of 10:1, in some embodiments exceeding approximately 100:1, and in other embodiments at least about 1000:1. At the top end, the aspect ratio could be indefinitely high but generally would be less than about 1,000,000:1. The hydraulic radius of a channel is no greater than about 300 micrometers. In many embodiments, it can be less than 100 micrometers, and may be less than 10 micrometers. Although smaller is generally better for many applications (and the hydraulic radius could be submicron in size), the hydraulic radius typically would not be less than 1 micrometers for most embodiments. As more fully described below, channels defined within these parameters can provide efficient bulk liquid transport through an active fluid transport device.

The structured surface can also be provided with a very low profile. Thus, active fluid transport devices are contemplated where the structured polymeric layer has a thickness of less than 5000 micrometers, and possibly less than 1500 micrometers. To do this, the channels may be defined by peaks that have a height of approximately 5 to 1200 micrometers and that have a peak distance of about 10 to 2000 micrometers.

Microstructured surfaces in accordance with the present invention provide flow systems in which the volume of the system is highly distributed. That is, the liquid volume that passes through such flow systems is distributed over a large area. Microstructure channel density from about 10 per lineal cm and up to about 1,000 per lineal cm (measured across the channels) provide for high liquid transport rates. Generally, when a manifold such as shown in FIG. 3a is employed, each individual channel has an aspect ratio that is at least 400 percent greater, and more preferably is at least 900 percent greater than a manifold that is disposed at the channel inlets and outlets. This significant increase in aspect ratio distributes the potential's effect to contribute to the noted benefits of the invention.

Suitable liquid channels for use in the present invention may be of any suitable geometry but are generally rectangular (typically having depths of 50 to 3000 micron and widths of 50 to 3000 micron or "V" channel patterns (typically having depths of about 50 to 3000 micron and heights of 50 to 3000 micron) with an included angle of generally 20 to 120 degrees and preferably about 45 degrees. The presently preferred structure has a nested construction wherein the master channels are 200 micron deep and repeat every 225 microns with three equally spaced channels in the base, each 40 microns deep. Compound channels are also possible and often preferably such as rectangular channels that contain smaller rectangular or "V" channels within.

Figure 2I:
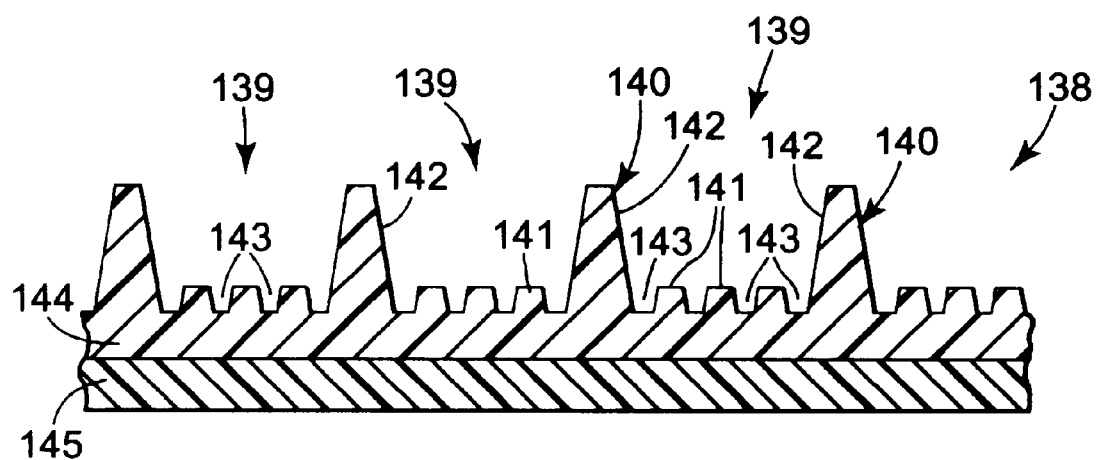
Figure 2J:
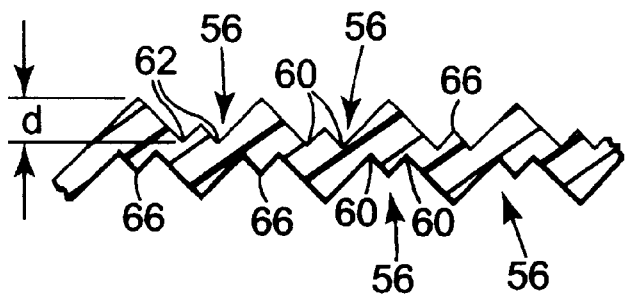
Figure 2K:
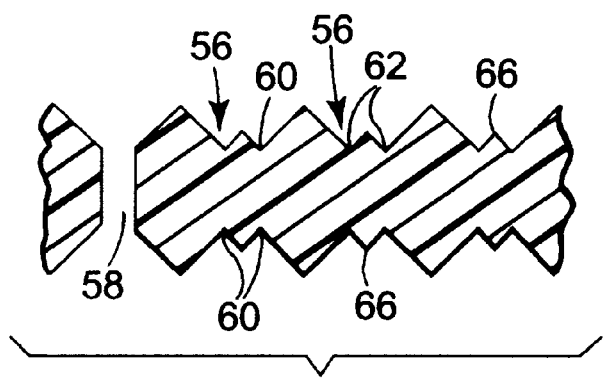

One preferred embodiment of a fluid transport film of the present invention is illustrated in FIG. 2i as alternate fluid control film 138. The film 138 has wide channels 139 defined between peaks 140. A plurality of smaller peaks 141 are located between side walls 142 of the peaks 140. The smaller peaks 141 thus define secondary channels 143 therebetween. The smaller peaks 141 are not as high as the peaks 140 and, as illustrated, create a first wide channel 139 including smaller channels 143 distributed therein.

Preferably, the center-to-center distance between peaks 140 is about 9 mils., and the center-to-center distance between peaks 141 is about 1.9 mils (the center-to-center distance between adjacent peaks 140 and 141 is about 2.6 mils). The walls of the peaks taper at an about 11° taper. Each peak is plateaued at its upper top with a lateral width of about 1 mil. At its base, the peak 140 has a width of about 2.5 mils., and at its base, the smaller peak 141 has a width of about 1.3 mils. The height of the peaks 140 is about 7.8 mils., while the height of the peaks 141 is about 1.6 mils. A body layer or backing layer 144 supports the peaks 140 and 141 and is made of the same material simultaneously via an extrusion process. The film 138 of FIG. 2i is formed from Tenite polyethylene 18BOA (available from Eastman Chemical Corporation, Kingsport, Tenn.) with 1% TRITON™ X-35 non-ironic surfactant. A second body layer 145 is bonded (e.g., by coextrusion) to the bottom side of the backing layer 144. The second body layer 145 is preferably formed from PE Eastman Tenite polyethylene 18BOA only (with no surfactant). Preferably, the nominal overall height of the fluid control film 138 is 11 mils, with the depth of the backing layer 144 being approximately being 1 mil., and the depth of the second layer 145 being approximately 2 mil. In an alternative embodiment, the total caliper (height) of the fluid control film 138 of FIG. 2i is 15 mil., with the additional height being provided by forming the peaks 140 to be taller. In addition, the fluid control film may include a tie layer on a bottom side thereof.

As mentioned previously, suitable fluid control film components of the present invention may be made through a process such as extrusion, injection molding, embossing, hot stamping, etc. In embossing, a substrate (e.g., a thermoplastic material) is deformed or molded. This process is usually performed at an elevated temperature and perhaps under pressure. The substrate or material is preferably made to replicate or approximately replicate the surface structure of a master tool. Since this process produces relatively small structures and is sometimes repeated many times over the process is referred to as microreplication. Suitable processes for microreplication are described in U.S. Pat. No. 5,514,120.

In one embodiment, the present invention relates to fluid control systems that incorporate fluid control film (e.g., microreplicated wicks) to move liquid from one area and transfer it to another, e.g., by capillary action. The presence of the fluid control film allows for a subfloor that can rapidly handle (e.g., absorb) large amounts of liquid from spills, leaks, and condensate, thus preventing corrosion of support beams caused by undesirable liquids. Specifically, the liquid control film component of the present invention serves to move liquid (such as spills) in food preparation or airline galley areas away from such areas in order to prevent corrosion (or, e.g., to move lavatory fluids in an airplane lavatory area to a collector in order to prevent corrosion).

Exemplary fluid transport systems of this invention are described herein and illustrate certain features of the present invention. In one preferred active fluid transfer embodiment the system comprises: a fluid control film; an adhesive; a substrate for attachment thereto, a cap layer; a vacuum or potential source; and a liquid collection means. In one preferred passive fluid transfer embodiment the system comprises: a fluid control film; an adhesive; and a substrate for attachment thereto. The components of these systems and variations thereof are discussed in detail herein and further illustrated in the included examples. While a specific combination of components may be disclosed as a preferred embodiment, it is contemplated that the disclosed features of various embodiments may be combined to achieve the objectives of the claimed invention.

An optional absorbent may be used in articles of the present invention, e.g., to serve as a reservoir to collect liquid moved off or away from the spill or leak sites. The articles of this invention have the advantage of allowing a wide variety of product designs. Preferred designs can incorporate increased surface area of the absorbent material, thereby allowing for management of higher liquid volumes.

Suitable absorbent materials include fibrous textile type materials, including woven, non-woven, knit, and stitch bonded materials or absorbent foams. Alternatively, the absorbent can comprise an absorbent polymer such as a hydrocolloid or hydrophilic polymer such as a supersorber. The hydrocolloid (e.g., starch, modified cellulose, gelatin or other protein, polysaccharide, etc) or supersorber (e.g., modified starch, acrylates, starch/acrylate copolymers, acylamides and other vinyl polymers, etc.) may be immobilized in a matrix such as a hydrophobic matrix of conventional hydrocolloid dressings or may alternatively be part of a hydrophilic gel matrix (e.g., a UV or E-beam cured acrylate). The absorbent may also comprise both a fibrous textile and an absorbent polymer. The absorbent pad may optionally contain an antimicrobial agent.

Referring again to FIG. 2a for illustrative purposes, the layer 22 includes the structured surface 24 and the underlying body layer 26. The layer 22 may include one or more additional layers of material (such as layers 26a or 26b) on its side opposite the structured surface 24, or such additional layers or other materials may be embedded within the body layer 26. The body layer 26 (and possible additional layers or materials therein) constitute backings for the structured surface 24. Suitable backings for use in fluid control articles of the present invention include conventional backings known in the art including non-woven and woven fibrous webs, knits, films, foams and other familiar backing materials. Preferred backings include thin (e.g., less than about 1.25 mm and preferably less than about 0.05 mm) and elastomeric backings. These types of backings help ensure conformability and high adhesion of the inventive fluid transport layer to and over substrate surface irregularities. Preferred backing materials include polyurethanes (e.g., ESTANE), polyether polyesters (e.g., HYEL), polyether amides (e.g., PEBAX) as well as polyolefins (e.g., ENGAGE, low density polyethylene). Another useful backing would also incorporate a flame retardant material. A multilayer approach could be used to provide a microreplicated film by coextrusion of multiple layers, one or more being flame retardant (such as disclosed in Kollaja et al., PCT International Publication No. WO 99/28128) and maintaining surface hydrophilicity.

Suitable adhesives for use in fluid transport articles of the present invention include any adhesive that provides acceptable adhesion to a variety or polar and non-polar substrates. Preferred adhesives are pressure sensitive and in certain embodiments preferably repel absorption of aqueous materials and do not contribute to corrosion. Suitable pressure sensitive adhesives include those based on acrylates, polyurethanes, KRATON and other block copolymers, silicones, rubber based adhesives (including natural rubber, polyisoprene, polyisobutylene, butyl rubber etc.) as well as combinations of these adhesives. The adhesive component may contain tackifiers, plasticizers, rheology modifiers as well as active components such as an antimicrobial agent. It is anticipated that removable liners may be used to protect the adhesive surface prior to use.

The preferred pressure sensitive adhesives which can be used in the adhesive composites of the present invention are the normal adhesives which are applied to various substrates, such as the acrylate copolymers described in U.S. Pat. No. RE 24,906, and particularly a 97:3 iso-octyl acrylate:acrylamide copolymer. Also preferred is an 65:35 2-ethylhexyl acrylate:isobornyl acrylate copolymer, and useful adhesives for this purpose are described in U.S. Pat. Nos. 5,804,610 and 5,932,298. Another useful adhesive could be a flame retardant adhesive. The inclusion of antimicrobial agents in the adhesive is also contemplated, as described in U.S. Pat. Nos. 4,310,509 and 4,323,557.

The structured surface may also be incorporated into an adhesive layer. In this case the adhesive must either be supported by a microreplicated liner having the mirror image of the fluid wick pattern or the adhesive must have sufficient yield stress and/or creep resistance to prevent flow and loss of the pattern during storage. Increase in yield stress is most conveniently accomplished by slightly crosslinking the adhesive (e.g., using covalent and/or ionic crosslinks or by providing sufficient hydrogen bonding). It is also understood that the adhesive layer may be discontinuous via the same methods, to allow for easy, bubble free application. Liners which are suitable for use in the adhesive composites of the present invention can be made of kraft papers, polyethylene, polypropylene, polyester or composites of any of these materials.

The liners are preferably coated with release agents such as fluorochemicals or silicones. For example, U.S. Pat. No. 4,472,480 describes low surface energy perfluorochemical liners. The preferred liners are papers, polyolefin films, or polyester films coated with silicone release materials. Examples of commercially available silicone coated release papers are POLYSLIK™ silicone release papers available from James River Co., H.P. Smith Division (Bedford Park, Ill.) and silicone release papers supplied by Daubert Chemical Co. (Dixon, Ill.). The most preferred liner is 1-60BKG-157 paper liner available from Daubert, which is a super calendared Kraft paper with a water-based silicone release surface.

Various modifications and alterations of this invention will become apparent to those skilled in the art without departing from the scope and spirit of this invention. All patents, patent applications and publications cited herein are incorporated by reference. Fluid transport devices of the present invention are applicable in numerous industrial and commercial applications. Structured surfaces having no cap layer (exposed to ambient conditions) are particularly suitable in evaporative and condensation collection applications, as well as gross fluid acquisition and removal applications. The fluid transport device with a cap layer has been found to be particularly suitable for use in flooring applications for acquisition and control of spilled liquids, thereby preventing corrosion to the underlying structure. Further specific applications and structures for the present invention are illustrated in the following examples.

EXAMPLES

Group I—Active Transport Examples

Example 1

Figure 7A:
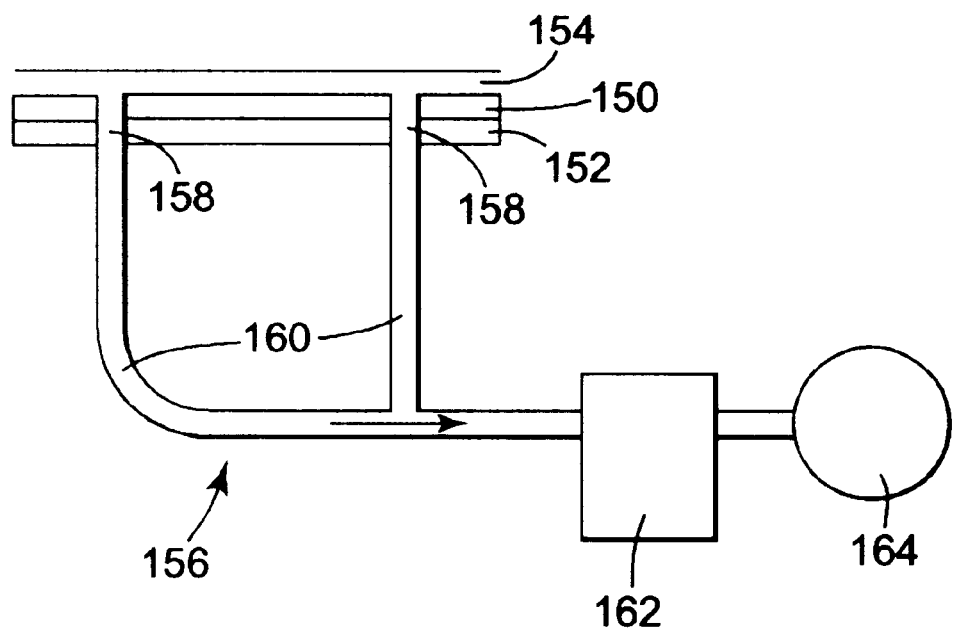
FIG. 7a is a schematic illustration of an alternative active fluid transport device of the present invention.
Figure 7B:
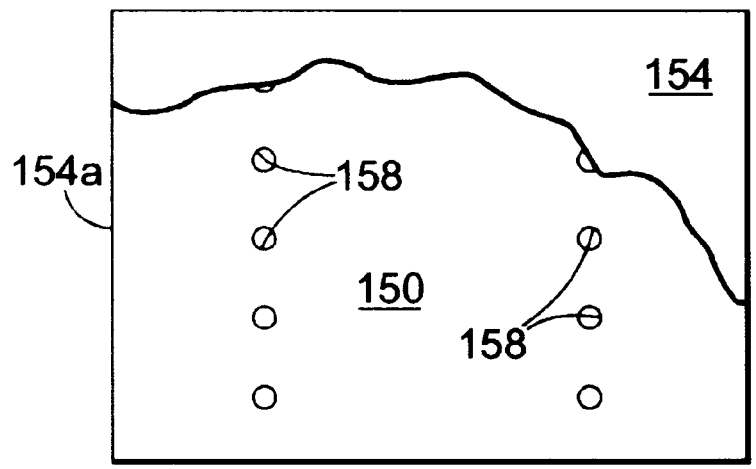
FIG. 7b is a plan view of the device of FIG. 7a, with the cap layer partially broken away for illustrative purposes.

A fluid removal system for use in collecting, transporting and removing fluid was formed from a flat, unstructured film adhered to a substrate. A potential was applied to enhance liquid movement across the film, with a cover layer applied over the flat film material. As seen in FIGS. 7a and 7b, the flat unstructured film was formed from a flat polyethylene film 150, adhered to a substrate 152 with a double-sided pressure sensitive adhesive and covered by a linoleum cap layer 154 (the cap layer 154 was not adhered to the film 150, just laid over it). A potential was provided by drawing a vacuum (six inches mercury) through a vacuum system 156 which included apertures 158, conduits 160, and a collection reservoir 162 and a vacuum pump 164. The vacuum allowed for continuous desiccation of the area under the film 150 to aid in collecting fluids spills thereon. The area tested was approximately 18 inches×36 inches, with ten drains or apertures 158 aligned in two rows, and spaced approximately 2 inches apart in each row. Each aperture 158 was 0.25 inch in diameter, while the conduits 160 had an ID of 0.375 inch. The distance between apertures and the size of the apertures can be maximized, depending on the strength of the vacuum potential applied.

The system of FIGS. 7a and 7b was tested by aligning the film 150 horizontally, and then by spilling 200 milliliters of water bearing red food coloring thereon. The system (substrate 152, film 150 and cap layer 154) was intended to simulate a flooring assembly on an airplane, and was tipped to one side for a short time period (such as side 154a) to simulate its orientation during landing or take-off of the airplane. There were no holes in the linoleum cap layer 154, so water disposed thereon went under the linoleum at its edges. In 10 minutes, 150 ml. of the water was collected in the liquid reservoir 162 (a 75% fluid removal and collection rate).

Example 2

Figure 8A:
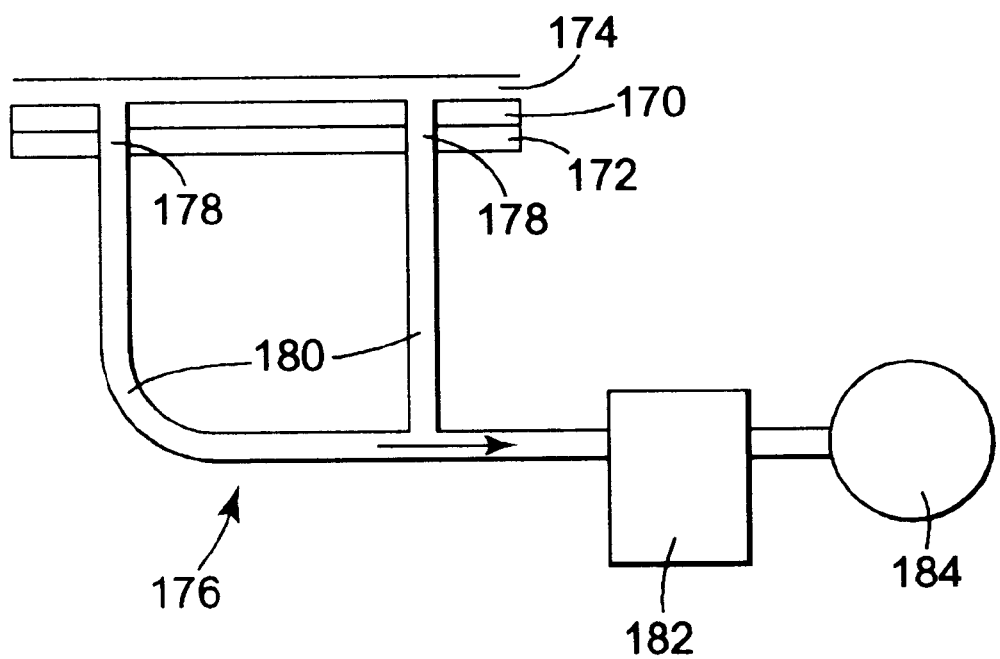
FIG. 8a is a schematic illustration of an alternative active fluid transport device of the present invention.
Figure 8B:
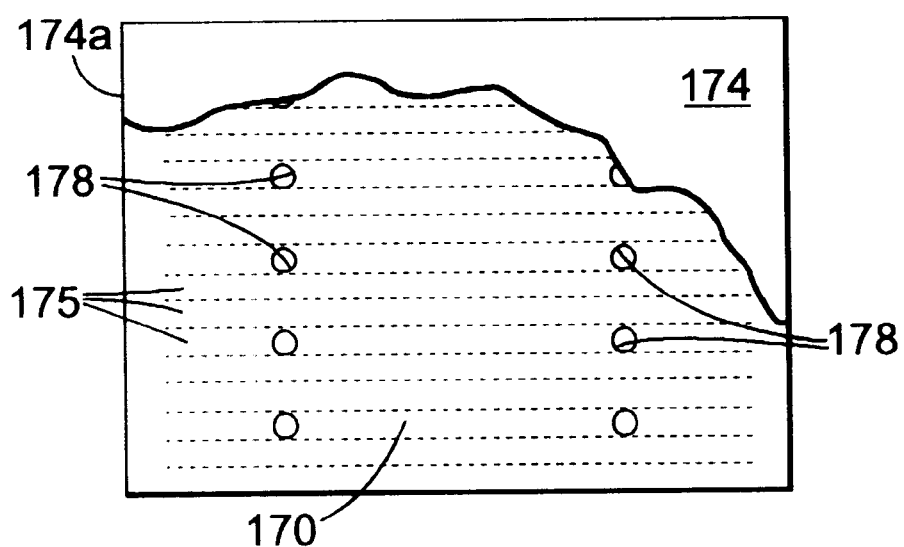
FIG. 8b is a plan view of the device of FIG. 5a, with the cap layer partially broken away for illustrative purposes.

A fluid removal system for use in collecting, transporting and removing fluid was formed from a fluid transport tape adhered to a substrate. This system was evaluated for use aerospace applications, and specifically for installation in airliner galley and lavatory applications (e.g., subfloors). The test arrangement of Example 2 was identical with that of Example 1 except for the substitution of a fluid control film for the flat polyethylene film 150. The fluid transport tape had a structured surface, and was formed of the material and configuration of the film 138 shown in FIG. 2i. A potential was applied across the fluid transport tape to enhance liquid movement, and a suitable cover was placed over the microstructured surface. The fluid transport tape was adhered by pressure sensitive adhesive to the passenger level flooring substrate. The adhesive comprised 65:35 2-ethylhexylacrylate (EHA): isobornylacrylate (IBOA), applied in a layer of about 2 mil. thickness. The suitable cover was again a cap layer of linoleum (unadhered to the fluid transport tape). Floor drains or apertures were installed and a vacuum (six inches mercury) applied. The vacuum allows for continuous desiccation of the area under the linoleum or carpet, and aids in collecting fluids spills. This system, as configured and tested, is illustrated in FIGS. 8a and 8b.

Fluid transport tape 170 was adhered to the flooring substrate 172 by the pressure sensitive adhesive, and covered by the cover 174. A liquid removal system 176 had apertures 178 in the fluid transport tape 170 and the substrate 172, fluidly connected to conduits 180, which in turn were connected to a liquid reservoir 182 and vacuum pump 184. The structured surface of the tape 170 included a plurality of grooves or channels 175 (FIG. 8b), wherein at least some of the channels 175 were in fluid communication with the apertures 178.

The Example 2 system was tested for fluid removal by aligning it horizontally and spilling 200 milliliters of red water on the system. The system was again briefly tipped, such as toward side 174a, and in 10 minutes, 170 ml. of the water was collected in the liquid reservoir 182 (an 85% removal and collection rate).

Example 3

The fluid removal system illustrated in FIGS. 8a and 8b was modified by applying absorbent strips on top of the microstructured film and perpendicular to the channels. The system was otherwise as shown in FIG. 8a, and as modified in FIG. 9. Absorbent strips 185 were placed on top of the structured surface of the microstructured film 170 (under the cap layer 174) and perpendicular to the channels 175 thereon. The absorbent strips 185 connected the apertures 178 and allowed liquid to flow to the apertures from adjacent channels 175. Each strip was approximately 0.5 inch by 16 inches, and the material used in this example to connect the apertures was a paper cloth available from Kimberly-Clark Corporation, Irving, Tex., under the name WYPALL™. However, each strip could be formed from another paper product, cloth, a porous filter, sponge, spun bound, non-woven or other similar material (i.e., any material that has sufficiently small pore size to induce capillary wicking of the liquid).

Figure 9:
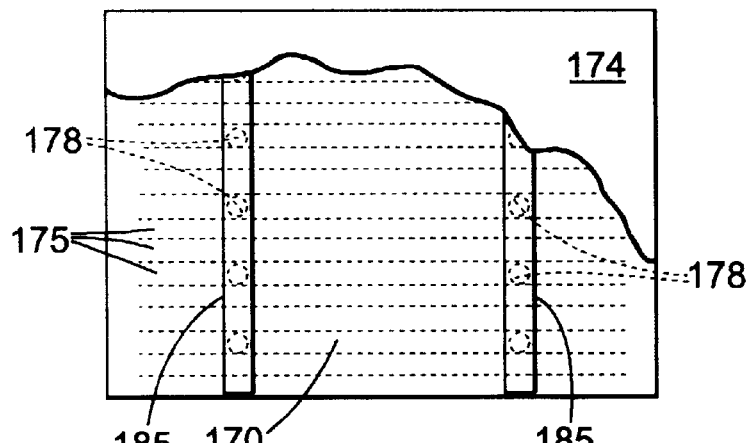
FIG. 9 is a plan view similar to FIG. 5b, with absorbent strips aligned between apertures, and with the cap layer partially broken away for illustrative purposes.

The system of FIG. 9 was tested for fluid removal by aligning it horizontally, spilling 170 milliliters of red water on the system and briefly tipping it. In 10 minutes, 155 ml. of water was collected in the liquid reservoir 182 (a 91% removal and collection rate).

Example 4

Figure 10:
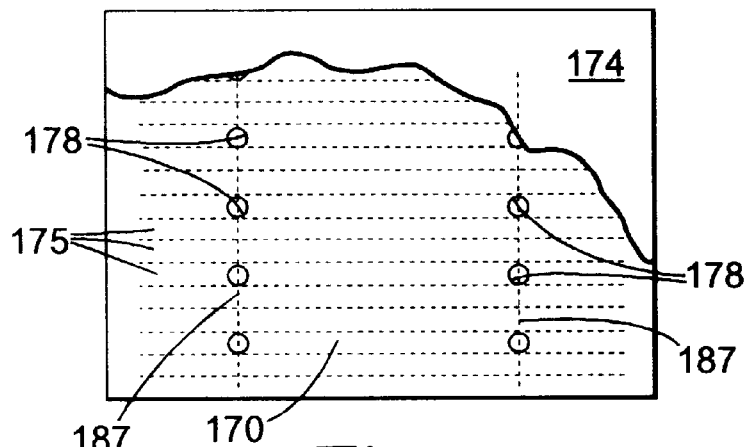
FIG. 10 is a plan view similar to FIG. 8b, with cross-channels formed between apertures, and with the cap layer partially broken away for illustrative purposes.

A fluid removal system set up such as shown in FIG. 8a was again tested, except that post-production embossed cross-channels were formed in the structured surface of the fluid transport tape. The cross-channels were formed using the edge of a heated metal plate of 0.1875 inch thickness (resulting in cross-channels approximately 0.125 inch wide), although a heated wire, hot knife or some other means for melting or embossing a cross-channel 187 (FIG. 10) in the structured surface 170 would suffice. The cross-channels 187 were formed after the fluid transport tape 170 was adhered to the substrate 172, and the cross-channels 187 extended perpendicular to the liquid transport film channels 175, as seen in FIG. 10. The purpose of the cross-channels 187 is to carry liquid to the apertures 178 from the channels 175 adjacent to each aperture 178.

The fluid removal system of Example 4 (FIG. 10) was tested for fluid removal by aligning it horizontally, spilling 200 milliliters of red water on the system and briefly tipping it. In 10 minutes, 190 ml. of water was collected in the liquid reservoir 182 (a 95% removal and collection rate).

As evidenced by a comparison of the removal and collection rates of Examples 1–4, providing apertures in communication with channels and then defining cross-channels significantly increases the removal and collection rate of water disposed on a horizontal surface. The microreplicated channels capture the water and provide a means for directing it to the cross-channels, which in turn are directed to the apertures. Providing post embossed cross-channels proved to be extremely effective in acquiring and removing spills, with all other conditions being constant among the tested examples.

Example 5

Figure 11:
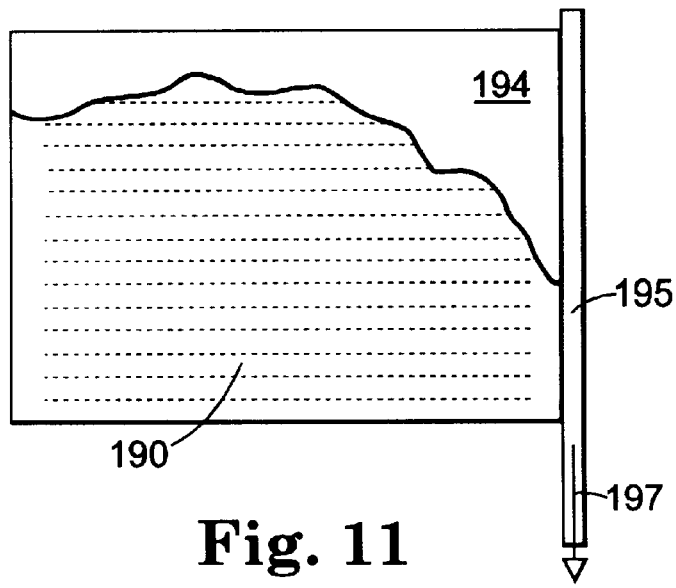
FIG. 11 is a plan view of an alternative active fluid transport device of the present invention, employing a side fluid collection manifold, and with the cap layer partially broken away for illustrative purposes.

A fluid removal system (another flooring system mockup) for use in collecting, transporting and removing fluid was defined by adhering a fluid transport tape 190 (FIG. 11) to a substrate (not shown). The tape 190 was the same as the tape 170 of Example 2, without the apertures therethrough, and was similarly adhered to the substrate. A suitable cover 194 (i.e., linoleum) was again laid over the fluid transport tape 190. In this example, no apertures are provided through the fluid transport tape 190. Rather, a drain manifold 195 was installed along one edge of the fluid transport tape 190 (in fluid communication with the channels 175 thereon) and a vacuum was applied (in direction of arrow 197). The vacuum allows for continued desiccation of the area under the linoleum (cover 194) and aids in collecting fluids spills.

While spill tests were conducted on the consturction of Example 5, no quantitive data was collected. It was observed, however, that the spilled liquid was aspirated under the cover toward the drain manifold for liquid movement and collection.

Group II—Passive Transport Examples

Figure 12A:
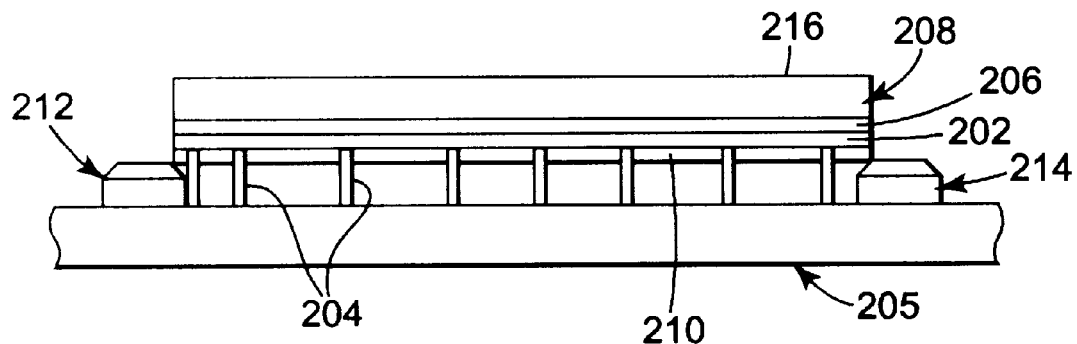
FIG. 12a is schematic illustration of a test assembly used for evaluating the collection and removal attributes of the present invention.

A fluid transport film adhered to a substrate was evaluated for use in collecting, transporting and removing liquids. The systems evaluated were designed for use in laptop computers, and specifically to be installed underneath the computer's keyboard to protect the hard goods of the computer from liquid spills and contamination. A side view schematic of the system is illustrated in FIG. 12a. A metal keyboard support plate 202 has a top side and a plurality of legs 204 extending from a bottom side thereof. The legs 204 are in turn supported upon a substrate or computer housing 205. A thin polyester sheet 206 extends over the top side of the metal plate 202, between the metal plate 202 and a bottom side of the keyboard 208.

Figure 12B:
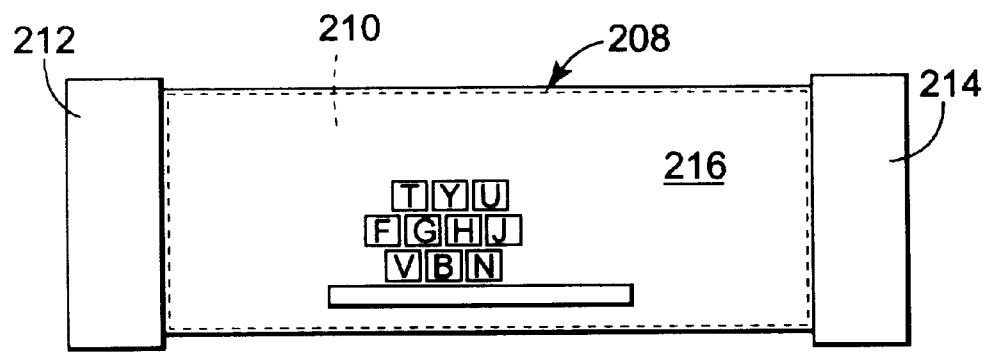

A spill test conducted on this assembly was evaluated using absorbent paper towels. A central paper towel assembly was positioned between the substrate 205 and the metal plate 202, such as towel assembly 210. Side paper towel assemblies 212 and 214 were aligned at the ends of the metal plate 202, on the substrate 205. FIG. 12b is a plan view of this arrangement, as viewed from a top surface 216 of the keyboard 208. The top surface 216 thus defines a drop zone for liquid spills, (underneath the keyboard 208, the polymer sheet 206 likewise has a drop or landing zone aligned for the reception of liquid from the keyboard 208 and, adjacent one or both ends of the polymer sheet 206, liquid removal zones are defined).

Example 6

In Example 6, the polymer sheet 206 is a flat unstructured polyester sheet disposed between the bottom of the keyboard 206 and the top of the metal plate 202. The polyester sheet had several holes pre-punched therein to accommodate attachment screws for holding the keyboard 208 to the metal support plate 202.

Example 7

In Example 7, the polymer sheet 206 is a fluid transport film having a structured surface on its upper face. The fluid transport film was the fluid transport tape of Example 2 (and FIG. 2i), with its channels longitudinally extending under the keyboard 208. The fluid transport film also had holes pre-punched through it to accommodate the fastener screws used to connect the keyboard 208 to the metal support plate 202.

Example 8

In Example 8, the same fluid transport film was used as the polymer sheet 206 as in Example 7, except that the fluid transport film did not have any holes pre-punched or cut in it. The screws used to hold the keyboard 208 to the metal plate 202 were screwed right through the polymer sheet 206, which resulted in a good seal around those screws.

Spill Test

In order to evaluate the fluid removal systems of Examples 6, 7 and 8, a spill test was performed. One ounce (approximately 30 milliliters) of water bearing red food coloring was deposited on the keyboard's "G" key and allowed to sit for two minutes. The keys in the middle row of the laptop keyboard 208 were pressed and the keyboard 208 was tipped and lightly shaken. Observations were made and the amounts of fluid absorbed at the edges and underneath the keyboard 208 were recorded. The paper towels 210, 212 and 214 were used as a way to determine where the water was going. In an actual commercial application, these towels would not be present. However, some type of collection device may be used for a computer keyboard application, such as some type of reservoir, absorbent or other object to serve as a collection device for liquid. Further, any collected liquid may be conveyed to the edge of the computer and allowed to be absorbed or to flow outside of the computer housing.

In the spill test for Example 6, most of the water collected underneath the keyboard 208 and metal plate 202. Water poured out of the front and back of the keyboard 208 when it was tilted. Water was found on both the top and bottom of the polyester film 206, and water was found on the top surface of the metal plate 202.

In the spill test for Example 7, water collected on the sides and underneath of the keyboard 208 and metal plate 202. Water was able to get underneath the metal plate 202 because it was transported to the holes that were provided in the film 206 as clearance for the screws. No water poured out of the front or the back of the keyboard 208 when tilted. Water was found on both the top and bottom sides of the film 206, and water was found on the top surface of the metal plate 202.

In the spill test for Example 8, most of the water was collected in the back of the keyboard 208. No water poured out of the front or the back of the keyboard when it was tilted. Water was only found on the top of the microstructured film 206. No water was found on the top side of the metal plate (presumably because of the effective seal around the screws resulting from the absence of pre-punched holes around the screws).

The results of these spill tests are tabulated in Table 1 below. The amounts indicated in Table 1 represent those amounts (by weight) of water collected from the various sources indicated.

TABLE 1

Water Collected in Passive Transport Example Spill Tests
(by weight, in grams)

|  | On Metal Plate and Film | On Side Paper Towel 212 | On Bottom Paper Towel 210 | On Side Paper Towel 214 |
| --- | --- | --- | --- | --- |
| Example 6 | 4 | 0 | 14 | 4 |
| Example 7 | 5 | 9.3 | 8.7 | 2 |
| Example 8 | 4 | 2 | 11 | 4 |

In the fluid collection devices of Examples 6, 7 and 8, no cap layer was provided (although a porous cap layer or filter may be useful in laptop applications such as, for example, a nonwoven porous filter adhered over the structured surface). As evidenced by the spill test observations and data, the use microreplicated structured surfaces for water collection and removal can significantly limit the exposure of adjacent components to moisture. In the spill test for Example 8, where the microstructured film had no pre-punched holes therein, no water was found on the top side of the metal plate, meaning that no water went through the microstructured surface—it was all captured thereon and diverted. In a commercial application of the inventive assembly, the microstructrured film is preferably affixed to its support substrate by a pressure sensitive adhesive.

Group III—Evaporative Enhancement Utilizing Microstructured Materials

Figure 13:
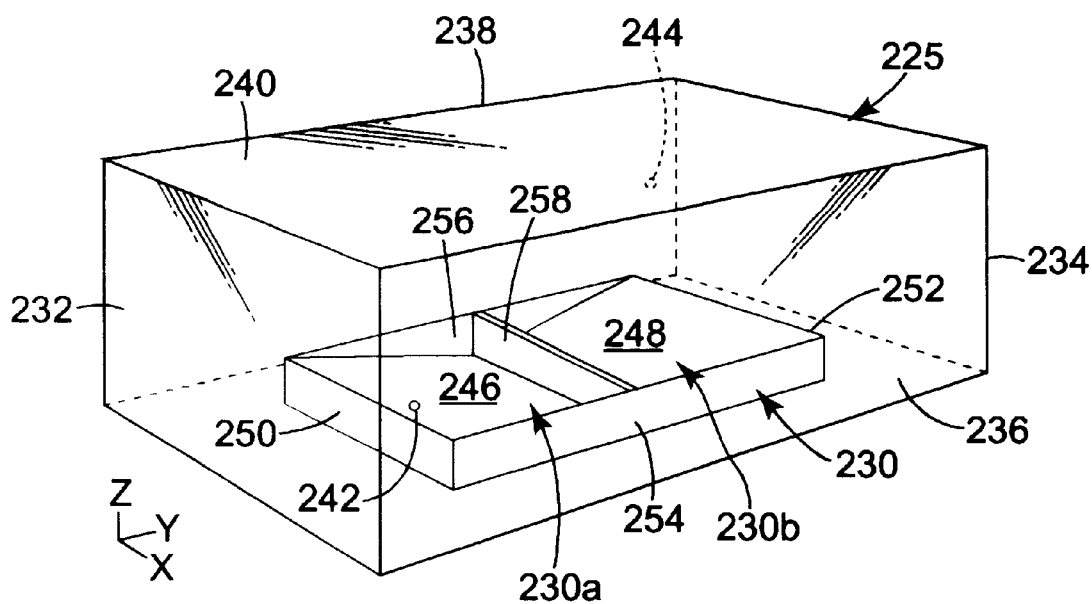
FIG. 13 is a perspective view of a test assembly for evaluating the evaporative attributes of the present invention.

In another test to evaluate the inventive fluid transport tape, an environmental test bed was created to measure the weight loss of water on the structured surface of the tape due to evaporation. The major components of this test system are illustrated in FIG. 13, and include an environmental control box 225, a sloped liquid reservoir 230, and a data acquisition system (not shown).

The control box 225 was a five-sided construction box (a box with an open bottom) made out of transparent Lexan plastic to have the following dimensions: 76 cm wide by 122 cm long by 41 cm deep. The box had end panels 232 and 234, side panels 236 and 238, and a top panel 240. The panels were sealed together along their contiguous edges. A dry air inlet hole 242 was formed in the side panel 236, twenty cm up from the bottom of the box and five cm from the end panel 232. An air outlet hole 244 was formed in the side panel 238 in a likewise position relative to the end panel 234. Dry air was provided to the box 225 at a rate of two cubic feet per minute by connecting a lab air supply to a desiccant column, and then connecting by conduit that column to the box 225, via inlet hole 242. The outlet hole 244 was left at ambient pressure to allow for outward airflow from the box 225.

The fluid reservoir 230 was formed to define two test bed floors 246 and 248 slopping upwardly and away from each other. The test bed floors and other portions of the fluid reservoir were formed from GILLFLOOR® 4017T light weight aircraft flooring panels, available from M.C. Gill Corporation, El Monte, Calif. The floors 246 and 248 were smooth and flat, and were supported by end panels 250 and 252, and side panels 254 and 256. A central lateral panel 258 ran across the "V"-groove to divide the fluid reservoir into two side-by-side, mirror image reservoirs 230a and 230b. The fluid reservoir 230 was 76 cm long, 44 cm wide and aligned with each floor 246 and 248 at a slope of 11° relative to horizontal, with a depth of eight cm adjacent the central panel 260 and a depth of zero cm adjacent the end panels 250 and 252. Room temperature water was poured into each reservoir 230a and 230b at the start of each evaporation experiment. The volume of water was measured out to be 100 cubic centimeters, 50 cc for each of the two side-by-side reservoirs. The fluid reservoir 230 was configured to simulate the components in an aircraft wing well, which are subject to corrosion caused by the unintended collection of liquids because of their cooperative and sloped geometries (which in part define a V-shaped sump).

The data acquisition system was based upon an Ohaus GT 4800 mass balance with an RS-232 serial interface. The mass balance was connected to a personal computer via the serial port. A custom Visual Basic application was used to periodically query the mass balance and record the reading on the computer. The balance was tared when the fluid reservoir was placed upon it, and then the water was added and mass measurements were recorded until the water was completely evaporated. A small, hand-held humidity and temperature monitoring device was placed in the control box to provide values for those conditions during the experiment.

Example 9

In Experiment 9, the mass loss of water versus time was recorded for the fluid reservoir 230 when contained inside the control box 225, starting with an initial volume of liquid of 100 cc. Various surface areas of fluid transport tape were applied to the fluid reservoir by centering the tape widthwise and running it from one end along the floors 246 and 248 down the middle of each floor, from the central panel 262 to each floor's respective end panel. The widths chosen for the fluid transport tape were zero (no film), five inches, ten inches and 15 inches. The composition and topography of the fluid transport film was the same for each of these experimental runs, and was the same as used in Example 2 (FIG. 2i). The pressure sensitive adhesive used to adhere the film to the test bed floor was also the same as set forth in Example 2.

Figure 14:
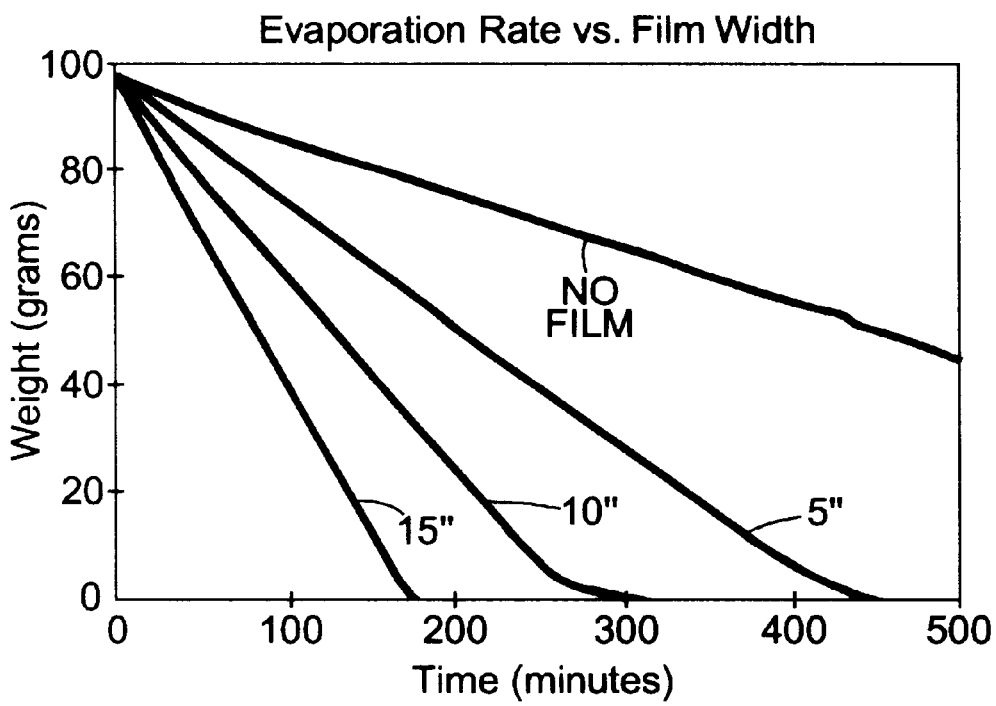
FIG. 14 is a graph of tested evaporation rates.

Table 2 presents the evaporation rate (in grams/minute) attained for each of the different film configurations tested, along with the initial and final temperatures and humidity. The actual mass loss for each film configuration was recorded and is shown in FIG. 14, which is a plot of the evaporation rate curves actually measured (evaporation rate in the form of weight loss over time).

TABLE 2

Experimental Data for Varying Film Widths and a Controlled Environment

| Film Width | Initial Humidity/ Temp | Final Humidity/ Temp | Evaporation Rate |
| --- | --- | --- | --- |
| No Film | 41% and 24 Celsius | 11% and 24 Celsius | 0.10 g/min. |
| 5 inches | 41% and 24 Celsius | 31% and 23 Celsius | 0.23 g/min. |
| 10 inches | 62% and 24 Celsius | 62% and 23 Celsius | 0.36 g/min |
| 15 inches | 62% and 24 Celsius | 62% and 22 Celsius | 0.57 g/min |

Example 10

Figure 15:
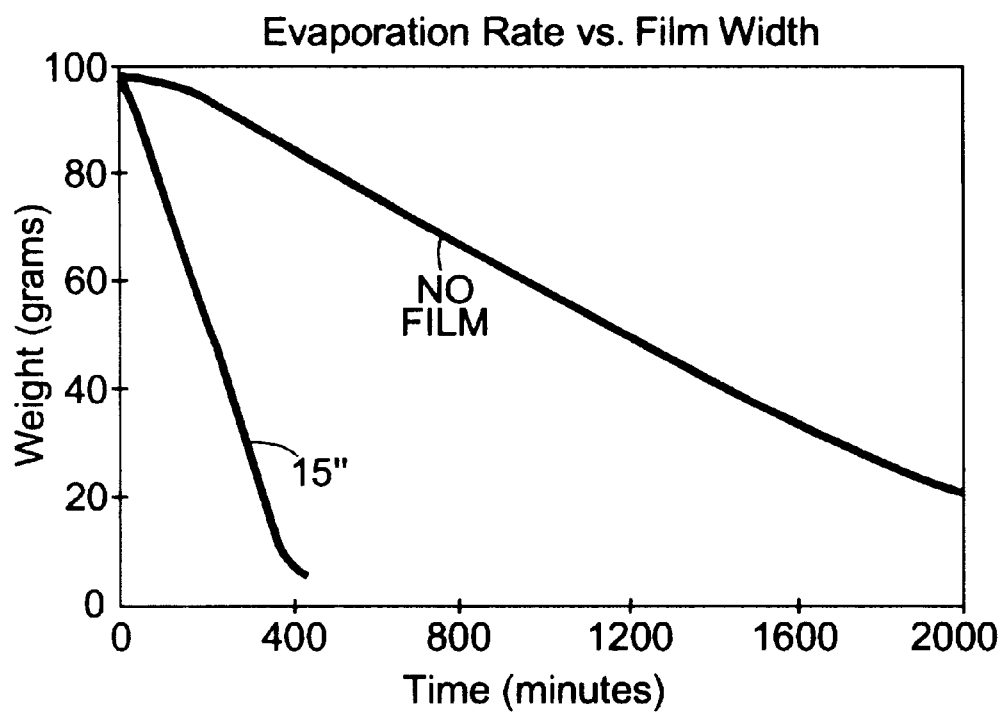
FIG. 15 is a graph of tested evaporation rates.

In Experiment 10, the mass loss versus time was recorded for the fluid reservoir 230, but the control box 225 was not used. In other words, the fluid reservoir 230 was tested in the open air environment of a lab. An initial liquid volume of 100 cc was introduced onto the fluid reservoir 230 as described in Example 9 above, and the evaporation rate was measured in the case of no film versus a 15 inch wide film. Temperature and humidity conditions were not recorded because the environment could not be controlled, but the tests of these two film conditions were evaluated on the same day to minimize macroscopic differences. FIG. 15 illustrates the data collected regarding weight loss of liquid over time. An evaporation rate of 0.041 grams/min. was achieved in the no film condition, while an evaporation rate of 0.24 grams/min. was achieved using a 15 inch wide film bearing a structured surface. These experiments thus confirm the remarkable improvement in the evaporation rate in the passive application of the fluid transport tape of the present invention. It is believed that evaporation has increased significantly because the surface area of the liquid exposed to the atmosphere is significantly increased on a structured surface having channels. The liquid evaporated from the microstructured film surface can, of course, be water (as in the above examples), but also can be other liquid materials depending upon the application. For example, the liquid could be ink or lubricants, or the liquid could be a fragrance or a fuel, or any combination of these types of liquids and characteristics.

Figure 16A:
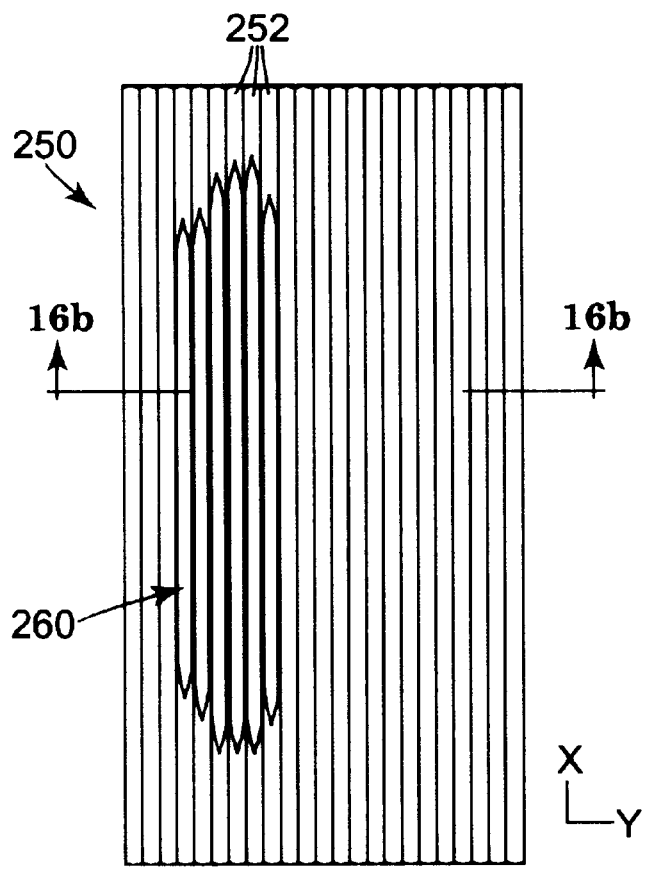
FIG. 16a is a schematic illustration of a channeled microstructured surface of the present invention with a quantity of liquid thereon.
Figure 16B:
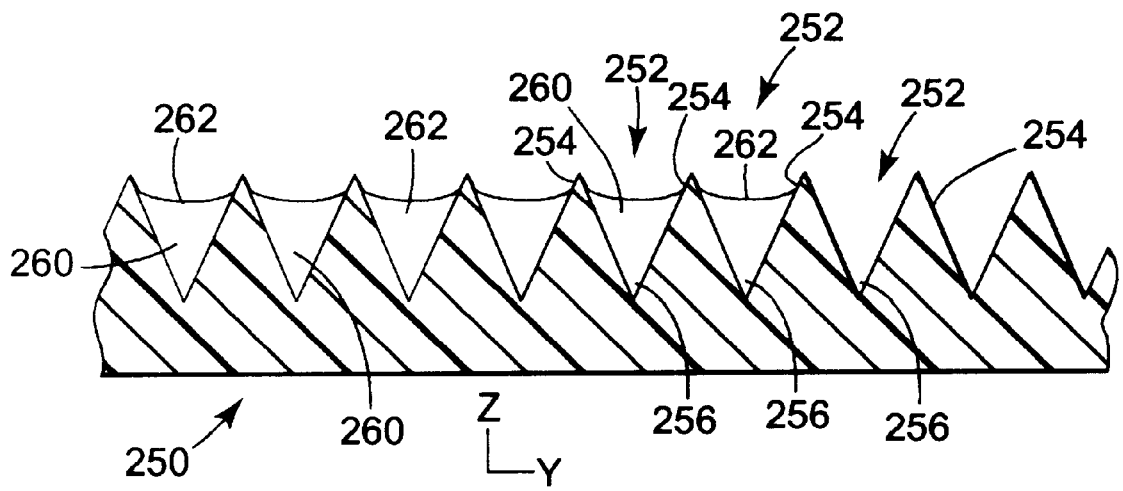

FIGS. 16a and 16b are illustrative of fluid flow effects across the face of a structured surface having a plurality of parallel channels, and specifically, of the increase in exposed fluid surface area achieved when a liquid is disposed on the structured surface of the present invention. A structured surface 250 having a plurality of channels 252 defined thereon has a liquid introduced thereon. In this exemplary illustration, the structured surface has a topography similar to FIG. 2a, with alternating peaks 254 and valleys 256. A liquid 260 introduced onto the structured surface 250. The channels 252 are formed to spontaneously wick the liquid along each channel which receives liquid therein to increase the spacial distribution of the liquid in the x-direction. As the liquid 260 fills each channel 252, its spacial distribution is also increased in the y-direction between the ridges of each channel 252, and the meniscus height of the liquid 260 varies in the z-direction within each channel 252, as seen in FIG. 16b. Adjacent each ridge, the liquid's exposed surface 262 is higher. These effects in three dimensions serve to increase the exposed evaporatively active surface area of the liquid 260, which, in turn, has the effect of enhancing the evaporation rate of the liquid 260 from the structured surface 250. As seen by the test results, the evaporation rate is increased significantly by the amplification of the "wetting" of the liquid on the surface as a result of the liquid spontaneously wicking along the micro-structured channels, and by the further amplification of the meniscus of the liquid in each channel. The end result is a superior exposure of the surface area of the liquid to ambient atmospheric conditions. The evaporation rate can be further enhanced by introducing a moving air stream across the top of the liquid 260 and structured surface 250.

Although not tested specifically above above, the inventive microstructured film surface also has beneficial effects for condensation applications (acquiring moisture from ambient as opposed to evaporation, where moisture is released to ambient). Both phenomena include a thermal energy component. For condensation to occur, the liquid landing zone on the microstructured film surface is at a temperature sufficiently lower than ambient to cause liquid to condense on the channels thereof. Once liquid has so condensed, the channels then serve to control liquid flow and divert the collected liquid to a suitable liquid removal zone for collection or further handling.

Group IV—Heat and Mass Transfer Enhancement Via Polymeric Microstructure Film Assemblies As noted, the microstructured surfaces of the present invention can be used to enhance mass transfer during evaporation, as well as during condensation. These examples illustrate how the rate of evaporation is enhanced by using a microstructured surface film assembly, as opposed to non-structured material surfaces in the case of active fluid flow and also in the presence of active air flow over the surfaces. The fluid transport film can be presented to the liquid flow by any means, including on a support structure or any self-supported assembly. The resulting noted benefits include evaporative cooling effects, humidification, evaporation, as well as condensation removal from a gas stream.

In evaporative cooling, many methods have been employed to efficiently cool water through evaporation. The main industrial application for evaporative cooling is air-water contacts to cool large quantities of water, since many processes require a coolant at a temperature below the prevailing summer temperatures of available surface waters. Relatively small amounts of water are cooled by spray ponds, while larger amounts, up to 100,000 gallons/minute, are cooled in cooling towers. In a cooling tower, water cascades downwardly over a fill pack, which is a structure designed to impede the direct fall of water streams and to increase the surface area of the water exposed to ambient, often by breaking up the water into drops. Open passages are provided in the fill packs for the flow of air over the exposed surface area of the water. The air-flow may be cross-wise, upward and counter current to the water flow, or a combination of both. Fill packs formed of wood slats, plates and plastic honeycomb structures have been used to spread out the air/liquid interface to both improve the mass transfer rate as well as to minimize liquid entrainment into the air stream. In evaporators, vacuums and plates have been used to increase the rate of evaporation. In some evaporative systems, a liquid is sprayed to produce more interfacial area partitioning the liquid and gas. Examples of prior art, gas/liquid contact assemblies (for evaporative coolers, humidifiers, heat exchangers, etc.) are illustrated in U.S. Pat. Nos. 3,792,841, 3,395,903, 3,500,615, 5,055,239 and 5,811, 035.

In this invention, the interfacial area is increased based upon the wetting out of the microreplicated film surface, and the entrainment of the liquid phase in the gas stream is minimized due to increased surface attachments (i.e., the increased contact area between the structure and the liquid). Experiments showed that in some cases, 100% improvement in mass transfer can be achieved, compared to non-microstructured surfaces, and that the added solid/liquid interface provides for added liquid attachment which will decrease the likelihood of air entrainment of the liquid. In other applications (e.g., humidification), foams and fibrous structures like pleated papers are often used as the liquid support surface. In these applications, scaling of non-volatile components typically builds up on the surface, which leads to the growth of organisms and decreased humidification performance. Using the microstructured film of the present invention, such scaling can be easily cleaned off or removed. With respect to the growth of algae and/or bacteria, antimicrobial agents can be impregnated into the film material to prevent the growth thereof.

In the case where an entrained mist or fog is to be coalesced, the present invention presents a means whereby a liquid encounters a high surface area media which allows the liquid droplets to attach to the surface more effectively than to a smooth surface. Wicking action along the surface of the microstructured media facilitates liquid flow, without obstructing the flow of liquid through the condensate collection device, thereby minimizing pressure drop across the media and efficiently channeling water in a desired manner to a desired location.

In one preferred embodiment, the invention is an assembly for enhancing the rate of evaporation of a liquid moving over a surface which comprises a film having first and second surfaces and means for causing the liquid to move across the first surface of the film. The first surface is a polymeric microstructure-bearing surface having channels thereon and is adapted for supporting a moving liquid thereon. The channels are defined by generally spaced apart protrusions with valleys therebetween so that the exposed evaporatively active surface area of the liquid on the first surface is increased by meniscus height variations of the moving liquid in each channel. The means for causing the liquid to move may comprise any suitable potential generating structure or system, such as a pump, pressure differential, gravity, etc., or any combination thereof.

In the following examples, the channels on the fluid transport film were parallel and orientated in the direction of liquid flow. However, this need not always be the case. Additional options for relative channel and liquid flow orientations are possible, including channels that extend orthologically relative to the fluid flow, or are biased relative to fluid flow direction, as well as the possibility of providing further projections from the micro-replicated surface to provide for increased interfacial surface area.

Figure 17A:
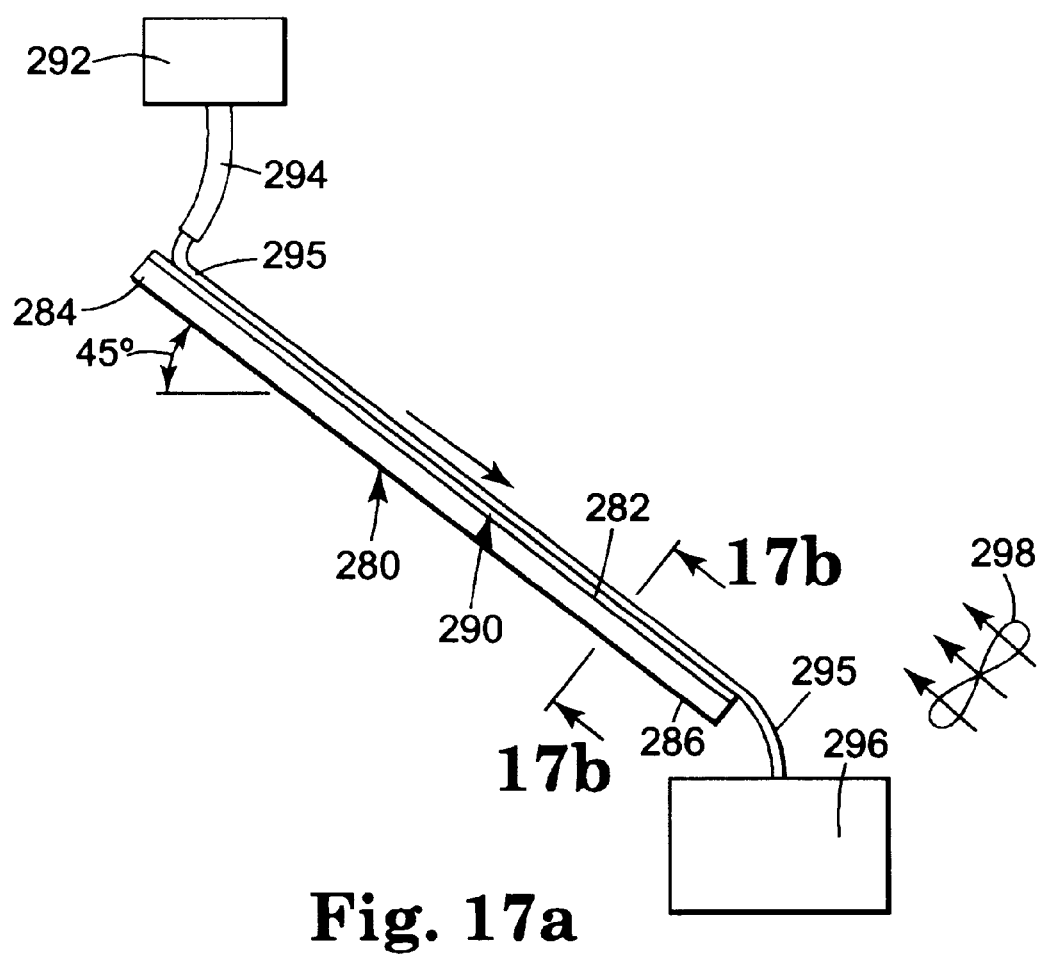
FIG. 17a is a schematic illustration of a test assembly used in evaluating the heat and mass transfer attributes of the present invention.

The evaporation or cooling rate of this group of experiments was determined using an experimental set-up that incorporated a 45° inclined plane substrate 280, as seen in FIG. 17a. The substrate 280 has a planar upper surface 282 with an upper end 284 and a lower end 286. A layer of polythene film 290 is aligned on the upper surface 282 of the substrate 280. In these experiments, the polythene layer 290 was not adhered to the upper surface 282; it was just laid out on the upper surface 282.

A water source 292 had a conduit 294 directed to deposit water 295 onto the film 290 adjacent the top end 284 of the substrate 280. The water 295 flowed down the film 290, was collected adjacent the bottom end 286 in a collection dam (not shown) and from there deposited into a collection reservoir 296. The film 290 in each instance was 4 inches wide, and the temperature of the water was measured at the top of the film, and then again at the bottom of the film. Air flow over the microstructured surface of the film 290 was provided using a standard carpet fan 298 positioned adjacent the bottom end 286 of the substrate 280. As shown, the air flow from the fan 298 was directed in the opposite direction of the water flow on the film 290. The air speed provided by the fan 298 was controlled by limiting the entrance area to the fan 298, and was measured using a hot wire anemometer adjacent the surface of the film 290.

The experiments using this system evaluated air speed effects, water flow rate and film surface microtopography. The data is presented as the water temperature differential between the top of the film and the bottom of the film, where the temperature of the water decreased as a function of the evaporation rate and associated latent heat of the water. The air was standard laboratory interior air, nominally at 70° F. and 50% relative humidity.

The following five materials were tested:

Example 12

A smooth polythene film contains a 0.5% TRITON™ X-100 additive by weight.

Example 13

A polythene film having a microstructured channel surface with linear channels. The polythene film contained a 0.5% TRITON™ X-100 additive by weight. The mold pattern tooling used to make the film's microstured surface had a pattern face formed to define channels with 45 degree groove angles β, 20 mil deep (see, e.g., FIG. 17b). The channels were aligned to run down the incline defined by the substrate 280.

Example 14

A polythene film contains a microstructured channel surface with linear channels. The polythene film contained a 0.5% TRITON™ X-100 additive by weight. The mold pattern tooling used to make the film's microstured surface had a pattern face formed to define channels with 80 degree groove angles, 10 mil deep. The channels were aligned to run down the incline defined by the substrate 280.

Example 15

Figure 18:
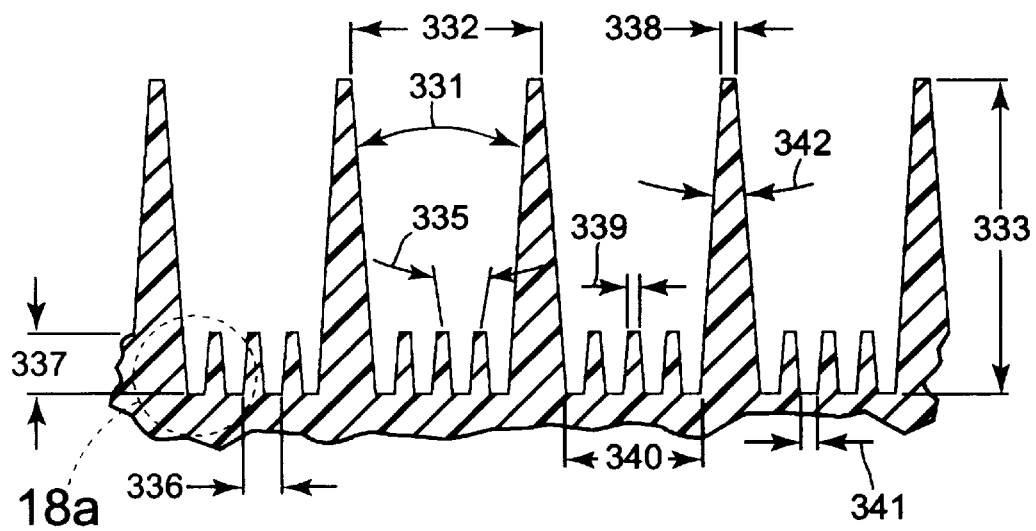
FIG. 18 is a cross-sectional cutaway view of the fluid control film of Example 15.
Figure 18A:
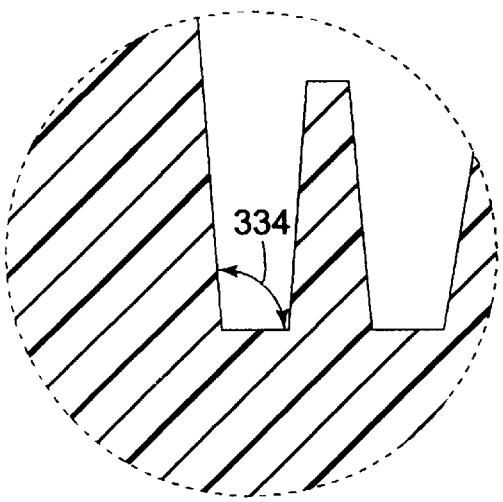
FIG. 18a is a blow-up of a portion of the fluid control film of FIG. 18.

A polythene film having a microstructured channel surface with linear channels. The polythene film contained a 0.5% TRITON™ X-100 additive by weight. The mold pattern tooling used to make the film's microstructured surface had a pattern face formed to define channels with nested rectangular channels, 8 mil deep. In cross section, this film had a configuration like the film of FIG. 18, and with four small rectangular shaped channels at the base of a larger rectangular shaped main channel (the same configuration as Pattern 5 in Table I of U.S. Pat. No. 5,728,446). The relative dimensions and angles for the microstructured polymer surface of this film is detailed as follows: primary groove angular width 331=10°, primary groove spacing 332=229 microns, primary groove depth 333=203 microns, notch included angle 334 (see FIG. 18a)=95°, secondary groove angular width 335=10°, secondary groove spacing 336=50 microns, secondary groove depth 337=41 microns, primary peak top width 338=29 microns, secondary peak top width 339=29 microns, primary groove base width 340=163 microns, secondary groove base width 341=13 microns, and primary groove wall angular width 342=10°. The channels were aligned to run down the incline defined by the substrate 280.

Example 16

A polythene film having a microstructured channel surface with linear channels. The polythene film contained a 0.5% TRITON™ X-100 additive by weight. The mold pattern tooling used to make the film's microstured surface had a pattern face formed to define channels with 40 degree groove angles, 45 mil deep. The channels were aligned to run down the incline defined by the substrate 280.

The five material samples of polythene film described above were tested under three dynamic air flow/water flow conditions, as follows:

Case 1—air flow at 152 meters/minute and water flow at 100 grams/minute

Case 2—air flow at 152 meters/minute and water flow at 330 grams/minute

Case 3—air flow at 305 meters/minute and water flow at 330 grams/minute

The results of the evaluation of the five Examples 12–15 under the conditions of Cases 1, 2 and 3 are detailed in Table 3 below.

TABLE 3

Active Evaporation Testing Results
(Change in Water Temperature (ΔT, in degrees Farenheit))

| | Case 1 | Case 2 | Case 3 |
|---|---|---|---|
| Example 12 | 0.7 | 0.65 | 1.0 |
| Example 13 | 1.8 | 1.2 | 1.7 |
| Example 14 | 1.8 | 1.4 | 1.4 |
| Example 15 | 1.9 | 1.5 | 1.3 |
| Example 16 | 1.6 | 0.6 | 1.3 |

As seen by a comparison of Example 12 (flat film) with Examples 13–16 (microstructured film), the use of the microreplicated structured surface in connection with active fluid and air flow for enhancing evaporation very significantly affects the rate of evaporation. In almost all instances, the evaporative rate is significantly increased relative to a smooth film surface under the same conditions. The relationship of opposed air flow and water flow rates is also illustrated, as well as a consideration of the topography of the microreplicated surface optimization for certain conditions.

Figure 17B:
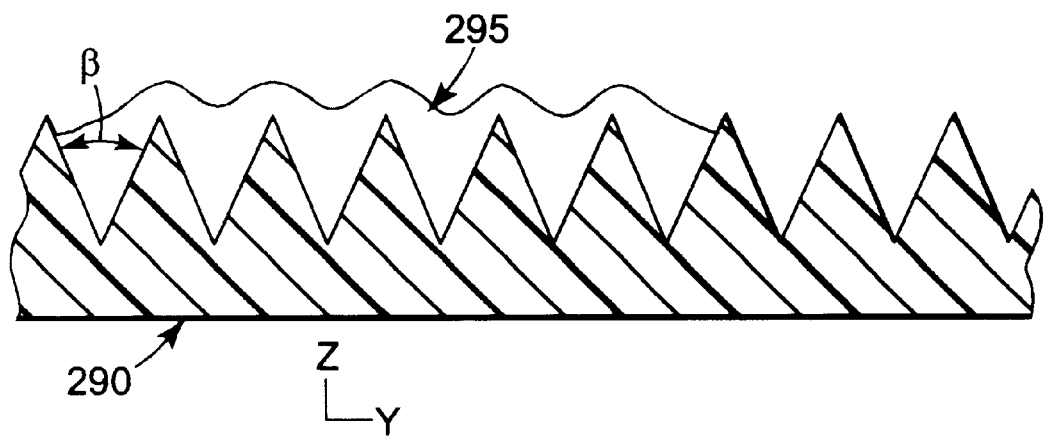

FIG. 17b illustrates the condition where the thickness of the liquid 295 on the microstructured film surface 290 is greater than the depth of the channels, thus communicating channels over adjacent ridges. In this situation, the microstructured surface of the film 290 still affects the exposed surface area of the liquid, forming undulations therein as the liquid 295 passes over the ridges. In this case, the thickness of the liquid is thin enough that it "sees" the film surface topography, and thus the microstructured surface has an effect on (enlarges) the surface area of the liquid 295 that is exposed to the ambient. As the liquid thickness increases, the undulations are less pronounced, and as a result, the effect of the topography on the exposed surface area of the liquid lessens. FIG. 17b illustrates one liquid flow rate over the film 290. If the flow rate is lessened, the thickness of the liquid 295 on the film 290 will decrease, and eventually assume the condition like that illustrated in FIG. 16b. In either event, as long as the thickness of the liquid is such that the topography of the microstructured surface affects the exposed surface area of the liquid (by affecting its wetting out characteristics and meniscus characteristics), liquid evaporation rates will be enhanced.

The present invention describes a fluid transport microstructured tape assembly. The microstructured surface provides a means to wick fluids that are aqueous or nonaqueous in nature. The surface can be comprised of a cast acrylic resin (for durability) or a polyolefin material. The adhesive provides a means to mount the tape to a structure in a manner that is consistent with desired fluid flow. The tape can be made with a variety of additives that, for example, make the tape flame retardant, hydrophillic, germicidal, hydrophobic, or capable of wicking acidic, basic or oily materials. The tape can utilize "V"-shaped or "U"-shaped or rectangular shaped micro structures (or combinations thereof) that are aligned in a radial intersecting, linear or any other custom or randomized pattern that is desired for optimal fluid flow in an industrial design. The tape can be used in active or passive applications. The active systems constitute a situation where a potential is applied across the tape surface and becomes a driving force for volume fluid movement. Active systems can be designed into applications with a manifold or other device that applies a potential across the tape surface, or can be placed to utilize existing sources of potential (i.e., wind or pressure differential). The tape can transport and remove fluid through capillary action by combination with a collection point such as a drain, absorbent material or collection pan. The tape can also be used to deliver fluids through the same capillary mechanism. The tape can also disperse fluid through evaporative mechanisms.

The inventive tape provides an attachment means that allows for negotiation over complex structures with minimal moisture ingress. The attachment means could be any means for attachment such as adhesive, mechanical, electrostatic, magnetic, or weak force attachment means. If the attachment means is an adhesive, the adhesive could be structural or pressure sensitive, and include the broad class of acrylates, non polar acrylates, synthetic rubber, polyolefin, or natural rubber. Mechanical attachment means could include plastiform, locking tapers, or hook and loop backings. The inventive tape can be used in a wide variety of industrial applications which benefit from fluid management, such as aerospace (i.e., reduction of corrosion by evaporative and collective mechanisms for fluid), turbine air compressors (from improvement in condensation knockout efficiency), oil separation in industrial processes, condensate removal in refrigeration, condensate collection efficiency in appliance applications, spill control in electronic applications (i.e., computer keyboards), deicing by means of continuous fluid removal, removal and/or collection of hazardous fluids (i.e., solvents, hydraulic fluids, acidic media or basic media), delivery of fluids with increased efficiency (e.g., inks, coatings, fuels, fragrances, etc.), removal of specific liquids (e.g., water, inks or other fluid sprays) from a surface, and detection of hazardous or non hazardous fluids by combination with detection devices.

In this disclosure several alternative embodiments of the invention are disclosed. It is understood that the features of these various embodiments may be compiled in any desired combination, configuration or assembly, depending upon the fluid flow application involved. As such, various modifications and alterations of this invention will become apparent to those skilled in the art without departing from the scope and spirit of the invention.

What is claimed is:

1. A laminate floor assembly comprising:
   a liquid control layer having a top side and a bottom side, the top side having a microstructure-bearing surface with a plurality of channels thereon that facilitate directional flow control of a liquid disposed thereon;
   a floor substrate layer;
   means for attaching the bottom side of the liquid control layer to the floor substrate layer;
   a cap layer having a top side and a bottom side, the bottom side of the cap layer being placed over the top side of the liquid control layer to define a relatively enclosed channel structure therebetween; and
   means for moving liquid along the channel structure defined between the top side of the liquid control layer and the bottom side of the cap layer.

2. The laminate floor assembly of claim 1 wherein the channels have first and second channel ends, and wherein the moving means withdraws the liquid from the channels adjacent the first channel end.

3. The laminate floor assembly of claim 2 wherein the moving means creates a potential which causes the liquid to move toward the first channel end for withdrawal.

4. The laminate floor assembly of claim 1, wherein the cap layer comprises:

a floor covering.

5. The laminate floor assembly of claim 4 wherein the floor covering is selected from the group consisting of carpet, tile, linoleum, wood, concrete, metal or fatigue matting.

6. The laminate floor assembly of claim 1 wherein the channels are defined by generally parallel ridges including a first set of ridges having a first height and a second set of ridges having a second, taller height.

7. The laminate floor assembly of claim 6 wherein an upper portion of each ridge of the second set of ridges has a lower melting temperature than a lower portion thereof.

8. The laminate floor assembly of claim 1 wherein the liquid control layer is a polymeric film.

9. The laminate floor assembly of claim 1 wherein the microstructure-bearing surface of the liquid control layer has a characteristic-altering coating thereon.

10. The laminate floor assembly of claim 8 wherein the polymeric film includes a characteristic altering additive.

11. The laminate floor assembly of claim 10 wherein the additive is selected from the group consisting of flame retardants, hydrophobics, hydrophylics, antimicrobial agents, inorganics, metallic particles, glass fibers, fillers, clays and nanoparticles.

12. The laminate floor assembly of claim 1 wherein the channels have a pattern geometry selected from the group consisting of linear, curvilinear, radial, parallel, non-parallel, random, or intersecting.

13. The laminate floor assembly of claim 1 wherein the cap layer is porous.

14. The laminate floor assembly of claim 13 wherein the cap layer is a non-woven.

15. The laminate floor assembly of claim 1 wherein the bottom side of the cap layer is affixed to the top side of the liquid control layer by a pressure sensitive adhesive.

16. The laminate floor assembly of claim 1 wherein the attaching means is a pressure sensitive adhesive.

17. The laminate floor assembly of claim 1 wherein the moving means creates a pressure gradient along the channel structure.

18. The laminate floor assembly of claim 1 wherein the top side of the liquid control layer has at least one cross-channel formed therein to facilitate liquid flow between the channels.

19. The laminate floor assembly of claim 18 wherein the liquid control layer has a liquid removal aperture therethrough which is in communication with the cross-channel and the moving means.

20. The laminate floor assembly of claim 1 wherein the top side of the liquid control layer has a plurality of cross-channels formed therein to facilitate liquid flow between the channels, and wherein the liquid control layer has a plurality of liquid removal apertures therethrough with each liquid moving aperture being in communication with one of the cross-channels and the moving means.

* * * * *

UNITED STATES PATENT AND TRADEMARK OFFICE
CERTIFICATE OF CORRECTION

PATENT NO.    : 6,531,206 B2
DATED         : March 11, 2003
INVENTOR(S)   : Johnston, Raymond P.

It is certified that error appears in the above-identified patent and that said Letters Patent is hereby corrected as shown below:

Column 2,
Line 66, after "thereof" insert -- . --

Column 6,
Line 1, "FIG. 5a" should read -- FIG. 8a --
Line 3, "FIG. 5b" should read -- FIG. 8b --

Column 29,
Line 56, delete the first instance of the word "above"

Signed and Sealed this

Twenty-ninth Day of June, 2004

JON W. DUDAS
*Acting Director of the United States Patent and Trademark Office*